US011624095B2

(12) United States Patent
Karn et al.

(10) Patent No.: US 11,624,095 B2
(45) Date of Patent: Apr. 11, 2023

(54) METHOD OF QUANTIFYING HIV RESERVOIRS BY INDUCED TRANSCRIPTION BASED SEQUENCING

(71) Applicant: CASE WESTERN RESERVE UNIVERSITY, Cleveland, OH (US)

(72) Inventors: Jonathan Karn, Cleveland, OH (US); Miguel Quinones-Mateu, Rocky River, OH (US); Curtis Dobrowolski, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 702 days.

(21) Appl. No.: 16/144,742

(22) Filed: Sep. 27, 2018

(65) Prior Publication Data
US 2019/0093182 A1 Mar. 28, 2019

Related U.S. Application Data

(60) Provisional application No. 62/564,098, filed on Sep. 27, 2017.

(51) Int. Cl.
| C12Q 1/70 | (2006.01) |
| A61K 39/21 | (2006.01) |
| A61K 31/565 | (2006.01) |

(52) U.S. Cl.
CPC ............ *C12Q 1/703* (2013.01); *A61K 31/565* (2013.01); *A61K 39/21* (2013.01); *C12Q 2600/16* (2013.01)

(58) Field of Classification Search
None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,803,227 | A | 2/1989 | Brandes et al. |
| 5,192,525 | A | 3/1993 | Yang et al. |
| 5,219,548 | A | 6/1993 | Yang et al. |
| 5,446,203 | A | 8/1995 | McNelis |
| 5,540,925 | A | 7/1996 | Mikulski et al. |
| 5,904,930 | A | 5/1999 | Fischer et al. |
| 6,096,874 | A | 8/2000 | Wallace et al. |
| 6,172,263 | B1 | 1/2001 | Double et al. |
| 7,018,994 | B2 | 3/2006 | Bohlmann et al. |
| 8,629,130 | B2 | 1/2014 | Yarger |
| 8,653,072 | B2 | 2/2014 | Rhonnstad et al. |
| 8,703,810 | B2 | 4/2014 | Kahraman et al. |
| 8,710,243 | B2 | 4/2014 | Hagberg et al. |
| 8,785,501 | B2 | 7/2014 | Witt-Enderby et al. |

OTHER PUBLICATIONS

2015 Towards an HIV Cure Symposium (brochure), Vancouver (13 pages). (Year: 2015).*
Poster Presentations; Journal of Virus Eradication 1(Supplement 1): 19-42. (Year: 2015).*
HIV Persistence during Therapy, Seventh International Workshop (brochure), Miami (12 pages). (Year: 2015).*
Karn, J. Estrogen blocks HIV re-emergence from latency and points to gender-specific differences in HIV reservoirs. (Slide set from oral presentation), IAS 2015 Towards an HIV Cure Symposium, Vancouver (14 pages). (Year: 2015).*
Lee et al. Quantification of the Latent HIV-1 Reservoir Using Ultra Deep Sequencing and Primer ID in a Viral Outgrowth Assay. J Acquir Immune Defic Syndr 74(2): 221-228. (Year: 2017).*
Zhou et al. Primer ID Validates Template Sampling Depth and Greatly Reduces the Error Rate of Next-Generation Sequencing of HIV-1 Genomic RNA Populations. Journal of Virology 89(16): 8540-8555. (Year: 2015).*
Crooks et al. Precise Quantitation of the Latent HIV-1 Reservoir: Implications for Eradication Strategies. JID 212: 1361-1365. (Year: 2015).*

* cited by examiner

*Primary Examiner* — Samuel C Woolwine
(74) *Attorney, Agent, or Firm* — Tarolli, Sundheim, Covell & Tummino LLP

(57) ABSTRACT

A method of determining the latent HIV reservoir level in a subject includes obtaining a blood sample from an HIV+ subject, isolating CD4+ T cells from the biological sample, administering one or more HIV transcription inducing agents to the isolated CD4+ T cells, isolating RNA from the CD4+ T-cells that includes HIV env mRNA, producing a plurality of first amplicons from the from the isolated RNA using a first primer set that corresponds to an HIV genomic region encoding the HIV env protein, producing a plurality of second amplicons from the plurality of first amplicons using a second primer set, the second primer set including one or more adapter sequences and/or uniquely identifiable barcode sequences, and determining the nucleic acid sequences of the second amplicons, wherein the determined nucleic acid sequences in the sample are indicative of the amount of inducible cell-associated HIV env RNA in the sample and indicative of the latent HIV reservoir in the subject.

24 Claims, 22 Drawing Sheets
Specification includes a Sequence Listing.

| Barcode Name-5' | Adapter | Barcode | Key | Primer | | | | |
|---|---|---|---|---|---|---|---|---|
| IonCode_0101 | CCATCTCATCCCTGCGTGTCTCCGACTCAG | CTAAGGTAAC | GGTGAT | caagcttctctatcaaagcag | 1 | IonCode_01 | IonCode_01_Fwd_A | CCATCTCATCCCTGCGTGTCTCCGACTCAGTAAGGTAACGGTGATcaagcttctctatcaaagcag | 67 | (SEQ ID NO: 5) |
| IonCode_0102 | CCATCTCATCCCTGCGTGTCTCCGACTCAG | TAAGGAGAAC | GGTGAT | caagcttctctatcaaagcag | 2 | IonCode_02 | IonCode_02_Fwd_A | CCATCTCATCCCTGCGTGTCTCCGACTCAGTAAGGAGAACGGTGATcaagcttctctatcaaagcag | 67 | (SEQ ID NO: 6) |
| IonCode_0103 | CCATCTCATCCCTGCGTGTCTCCGACTCAG | AAGAGGATTC | GGTGAT | caagcttctctatcaaagcag | 3 | IonCode_03 | IonCode_03_Fwd_A | CCATCTCATCCCTGCGTGTCTCCGACTCAGAAGAGGATTCGGTGATcaagcttctctatcaaagcag | 67 | (SEQ ID NO: 7) |
| IonCode_0104 | CCATCTCATCCCTGCGTGTCTCCGACTCAG | TACCAAGATC | GGTGAT | caagcttctctatcaaagcag | 4 | IonCode_04 | IonCode_04_Fwd_A | CCATCTCATCCCTGCGTGTCTCCGACTCAGTACCAAGATCGGTGATcaagcttctctatcaaagcag | 67 | (SEQ ID NO: 8) |
| IonCode_0105 | CCATCTCATCCCTGCGTGTCTCCGACTCAG | CAGAAGGAAC | GGTGAT | caagcttctctatcaaagcag | 5 | IonCode_05 | IonCode_05_Fwd_A | CCATCTCATCCCTGCGTGTCTCCGACTCAGCAGAAGGAACGGTGATcaagcttctctatcaaagcag | 67 | (SEQ ID NO: 9) |
| IonCode_0106 | CCATCTCATCCCTGCGTGTCTCCGACTCAG | CTGCAAGTTC | GGTGAT | caagcttctctatcaaagcag | 6 | IonCode_06 | IonCode_06_Fwd_A | CCATCTCATCCCTGCGTGTCTCCGACTCAGCTGCAAGTTCGGTGATcaagcttctctatcaaagcag | 67 | (SEQ ID NO: 10) |
| IonCode_0107 | CCATCTCATCCCTGCGTGTCTCCGACTCAG | TTCGTGATTC | GGTGAT | caagcttctctatcaaagcag | 7 | IonCode_07 | IonCode_07_Fwd_A | CCATCTCATCCCTGCGTGTCTCCGACTCAGTTCGTGATTCGGTGATcaagcttctctatcaaagcag | 67 | (SEQ ID NO: 11) |
| IonCode_0108 | CCATCTCATCCCTGCGTGTCTCCGACTCAG | TTCCGATAAC | GGTGAT | caagcttctctatcaaagcag | 8 | IonCode_08 | IonCode_08_Fwd_A | CCATCTCATCCCTGCGTGTCTCCGACTCAGTTCCGATAACGGTGATcaagcttctctatcaaagcag | 67 | (SEQ ID NO: 12) |

Fig. 7

| IonCode_0109 | CCATCTCATCCCTGC GTGTCTCCGACTCA G | TGAGCGGA AC | GGTGAT | caagtttctctat caaagcag | 9 | IonCode_09 | IonCode_09_Fwd_A | CCATCTCATCCCTGCGTGTCT CCGACTCAGTGAGCGGAACG GTGATcaagtttctctatcaaagca g | 67 | (SEQ ID NO: 13) |
|---|---|---|---|---|---|---|---|---|---|---|
| IonCode_0110 | CCATCTCATCCCTGC GTGTCTCCGACTCA G | CTGACCGA AC | GGTGAT | caagtttctctat caaagcag | 10 | IonCode_10 | IonCode_10_Fwd_A | CCATCTCATCCCTGCGTGTCT CCGACTCAGTGACCGAACG GTGATcaagtttctctatcaaagca g | 67 | (SEQ ID NO: 14) |
| IonCode_0111 | CCATCTCATCCCTGC GTGTCTCCGACTCA G | TCCTCGAA TC | GGTGAT | caagtttctctat caaagcag | 11 | IonCode_11 | IonCode_11_Fwd_A | CCATCTCATCCCTGCGTGTCT CCGACTCAGTCCTCGAATCG GTGATcaagtttctctatcaaagca g | 67 | (SEQ ID NO: 15) |
| IonCode_0112 | CCATCTCATCCCTGC GTGTCTCCGACTCA G | TAGGTGGT TC | GGTGAT | caagtttctctat caaagcag | 12 | IonCode_12 | IonCode_12_Fwd_A | CCATCTCATCCCTGCGTGTCT CCGACTCAGTAGGTGGTTCG GTGATcaagtttctctatcaaagca g | 67 | (SEQ ID NO: 16) |
| IonCode_0113 | CCATCTCATCCCTGC GTGTCTCCGACTCA G | TCTAACGG AC | GGTGAT | caagtttctctat caaagcag | 13 | IonCode_13 | IonCode_13_Fwd_A | CCATCTCATCCCTGCGTGTCT CCGACTCAGTCTAACGGACG GTGATcaagtttctctatcaaagca g | 67 | (SEQ ID NO: 17) |
| IonCode_0114 | CCATCTCATCCCTGC GTGTCTCCGACTCA G | TTGGAGTG TC | GGTGAT | caagtttctctat caaagcag | 14 | IonCode_14 | IonCode_14_Fwd_A | CCATCTCATCCCTGCGTGTCT CCGACTCAGTTGGAGTGTCG GTGATcaagtttctctatcaaagca g | 67 | (SEQ ID NO: 18) |
| IonCode_0115 | CCATCTCATCCCTGC GTGTCTCCGACTCA G | TCTAGAGG TC | GGTGAT | caagtttctctat caaagcag | 15 | IonCode_15 | IonCode_15_Fwd_A | CCATCTCATCCCTGCGTGTCT CCGACTCAGTCTAGAGGTCG GTGATcaagtttctctatcaaagca g | 67 | (SEQ ID NO: 19) |
| IonCode_0116 | CCATCTCATCCCTGC GTGTCTCCGACTCA G | TCTGGATG AC | GGTGAT | caagtttctctat caaagcag | 16 | IonCode_16 | IonCode_16_Fwd_A | CCATCTCATCCCTGCGTGTCT CCGACTCAGTCTGGATGACG GTGATcaagtttctctatcaaagca g | 67 | (SEQ ID NO: 20) |
| IonCode_0117 | CCATCTCATCCCTGC GTGTCTCCGACTCA G | TCTATTCGT C | GGTGAT | caagtttctctat caaagcag | 17 | IonCode_17 | IonCode_17_Fwd_A | CCATCTCATCCCTGCGTGTCT CCGACTCAGTCTATTCGTCGG | 67 | (SEQ ID NO: 21) |

Fig. 7 (Continued)

| IonCode Name | Adapter | Barcode | | | | | | | |
|---|---|---|---|---|---|---|---|---|---|
| IonCode_0118 | CCATCTCATCCCTGCGTGTCTCCGACTCAG | AGGCAATTGC | GGTGAT | caagcttctctatcaaagcag | 18 | IonCode_18_Fwd_A | CCATCTCATCCCTGCGTGTCTCCGACTCAGAGGCAATTGCGGTGATcaagcttctctatcaaagcag | 67 | (SEQ ID NO: 22) |
| IonCode_0119 | CCATCTCATCCCTGCGTGTCTCCGACTCAG | TTAGTCGGAC | GGTGAT | caagcttctctatcaaagcag | 19 | IonCode_19_Fwd_A | CCATCTCATCCCTGCGTGTCTCCGACTCAGTTAGTCGGACGGTGATcaagcttctctatcaaagcag | 67 | (SEQ ID NO: 23) |
| IonCode_0120 | CCATCTCATCCCTGCGTGTCTCCGACTCAG | CAGATCCATC | GGTGAT | caagcttctctatcaaagcag | 20 | IonCode_20_Fwd_A | CCATCTCATCCCTGCGTGTCTCCGACTCAGCAGATCCATCGGTGATcaagcttctctatcaaagcag | 67 | (SEQ ID NO: 24) |
| IonCode_0121 | CCATCTCATCCCTGCGTGTCTCCGACTCAG | TCGCAATTAC | GGTGAT | caagcttctctatcaaagcag | 21 | IonCode_21_Fwd_A | CCATCTCATCCCTGCGTGTCTCCGACTCAGTCGCAATTACGGTGATcaagcttctctatcaaagcag | 67 | (SEQ ID NO: 25) |
| IonCode_0122 | CCATCTCATCCCTGCGTGTCTCCGACTCAG | TTCGAGACGC | GGTGAT | caagcttctctatcaaagcag | 22 | IonCode_22_Fwd_A | CCATCTCATCCCTGCGTGTCTCCGACTCAGTTCGAGACGCGGTGATcaagcttctctatcaaagcag | 67 | (SEQ ID NO: 26) |
| IonCode_0123 | CCATCTCATCCCTGCGTGTCTCCGACTCAG | TGCCACGAAC | GGTGAT | caagcttctctatcaaagcag | 23 | IonCode_23_Fwd_A | CCATCTCATCCCTGCGTGTCTCCGACTCAGTGCCACGAACGGTGATcaagcttctctatcaaagcag | 67 | (SEQ ID NO: 27) |
| IonCode_0124 | CCATCTCATCCCTGCGTGTCTCCGACTCAG | AACCTCATTC | GGTGAT | caagcttctctatcaaagcag | 24 | IonCode_24_Fwd_A | CCATCTCATCCCTGCGTGTCTCCGACTCAGAACCTCATTCGGTGATcaagcttctctatcaaagcag | 67 | (SEQ ID NO: 28) |
| Barcode Name-3' | Adapter | Barcode | Key | Primer | | | | | |
| IonCode_ | CCTCTCTATGGGCA | CCTGAGAT | | tctgatgcacaa | 25 | IonCode_A_RVS_T | CCTCTCTATGGGCAGTCGGT | 55 | (SEQ ID NO: |

Fig. 7 (Continued)

| | | | | | | |
|---|---|---|---|---|---|---|
| IonCode_0125 | GTCGGTGAT | AC | aatagagtgg | | GATCCTGAGATACtctgatgcac aaaatagagtgg | | (SEQ ID NO: 29) |
| IonCode_0126 | CCTCTCTATGGGCA GTCGGTGAT | TTACAACCT C | tctgatgcacaa aatagagtgg | 26 | IonCode_B | IonCode_B_RVS_Tr P | CCTCTCTATGGGCAGTCGGT GATTTACAACCTctgatgcac aaatagagtgg | 55 | (SEQ ID NO: 30) |
| IonCode_0127 | CCTCTCTATGGGCA GTCGGTGAT | AACCATCC GC | tctgatgcacaa aatagagtgg | 27 | IonCode_C | IonCode_C_RVS_Tr P | CCTCTCTATGGGCAGTCGGT GATAACCATCCGCtctgatgcac aaatagagtgg | 55 | (SEQ ID NO: 31) |
| IonCode_0128 | CCTCTCTATGGGCA GTCGGTGAT | ATCCGGAA TC | tctgatgcacaa aatagagtgg | 28 | IonCode_D | IonCode_D_RVS_T rP | CCTCTCTATGGGCAGTCGGT GATATCCGGAATCtctgatgcac aaatagagtgg | 55 | (SEQ ID NO: 32) |
| IonCode_0129 | CCTCTCTATGGGCA GTCGGTGAT | CGAGGTTA TC | tctgatgcacaa aatagagtgg | 29 | IonCode_E | IonCode_E_RVS_Tr P | CCTCTCTATGGGCAGTCGGT GATCGAGGTTATCtctgatgcac aaatagagtgg | 55 | (SEQ ID NO: 33) |
| IonCode_0130 | CCTCTCTATGGGCA GTCGGTGAT | TCCAAGCT GC | tctgatgcacaa aatagagtgg | 30 | IonCode_F | IonCode_F_RVS_Tr P | CCTCTCTATGGGCAGTCGGT GATTCCAAGCTGCtctgatgcac aaatagagtgg | 55 | (SEQ ID NO: 34) |
| IonCode_0131 | CCTCTCTATGGGCA GTCGGTGAT | TCTTACACA C | tctgatgcacaa aatagagtgg | 31 | IonCode_G | IonCode_G_RVS_T rP | CCTCTCTATGGGCAGTCGGT GATTCTTACACACtctgatgcac aaatagagtgg | 55 | (SEQ ID NO: 35) |
| IonCode_0132 | CCTCTCTATGGGCA GTCGGTGAT | TTCTCATTGAAAC | tctgatgcacaa aatagagtgg | 32 | IonCode_H | IonCode_H_RVS_T rP | CCTCTCTATGGGCAGTCGGT GATTTCATTGAACtctgatgc acaaatagagtgg | 57 | (SEQ ID NO: 36) |
| IonCode_0133 | CCTCTCTATGGGCA GTCGGTGAT | TCGCATCGTTC | tctgatgcacaa aatagagtgg | 33 | IonCode_I | IonCode_I_RVS_Tr P | CCTCTCTATGGGCAGTCGGT GATTCGCATCGTTctctgatgca caaatagagtgg | 56 | (SEQ ID NO: 37) |
| IonCode_0134 | CCTCTCTATGGGCA GTCGGTGAT | TAAGCCATTGTC | tctgatgcacaa aatagagtgg | 34 | IonCode_J | IonCode_J_RVS_Tr P | CCTCTCTATGGGCAGTCGGT GATTAAGCCATTGTCtctgatgc acaaatagagtgg | 57 | (SEQ ID NO: 38) |
| IonCode_0135 | CCTCTCTATGGGCA GTCGGTGAT | AAGGAATCGTC | tctgatgcacaa aatagagtgg | 35 | IonCode_K | IonCode_K_RVS_Tr P | CCTCTCTATGGGCAGTCGGT GATAAGGAATCGTCtctgatgc acaaatagagtgg | 56 | (SEQ ID NO: 39) |
| IonCode_ | CCTCTCTATGGGCA | CTTGAGAATGTC | tctgatgcacaa | 36 | IonCode_ | IonCode_L_RVS_Tr | CCTCTCTATGGGCAGTCGGT | 57 | (SEQ ID NO: |

Fig. 7 (Continued)

| | | | | | | |
|---|---|---|---|---|---|---|
| 0136 | GTCGGTGAT | | aatagagtgg | | | GATCTTGAGAAATGTCtctgatgcacaaatagagtgg (SEQ ID NO: 40) |
| IonCode_0137 | CCTCTCTATGGGCAGTCGGTGAT | TGGAGGACGGAC | tctgatgcacaaaatagagtgg | 37 | IonCode_M | IonCode_M_RVS_TrP | CCTCTCTATGGGCAGTCGGTGATTGGAGGACGGACtctgatgcacaaatagagtgg 57 (SEQ ID NO: 41) |
| IonCode_0138 | CCTCTCTATGGGCAGTCGGTGAT | TAACAATCGGC | tctgatgcacaaaatagagtgg | 38 | IonCode_N | IonCode_N_RVS_TrP | CCTCTCTATGGGCAGTCGGTGATTAACAATCGGCtctgatgcacaaatagagtgg 56 (SEQ ID NO: 42) |
| IonCode_0139 | CCTCTCTATGGGCAGTCGGTGAT | CTGACATAATC | tctgatgcacaaaatagagtgg | 39 | IonCode_O | IonCode_O_RVS_TrP | CCTCTCTATGGGCAGTCGGTGATCTGACATAATCtctgatgcacaaatagagtgg 56 (SEQ ID NO: 43) |
| IonCode_0140 | CCTCTCTATGGGCAGTCGGTGAT | TTCCACTTCGC | tctgatgcacaaaatagagtgg | 40 | IonCode_P | IonCode_P_RVS_TrP | CCTCTCTATGGGCAGTCGGTGATTTCCACTTCGCtctgatgcacaaatagagtgg 56 (SEQ ID NO: 44) |

Fig. 7 (Continued)

SEQUENCE LISTING

<160> NUMBER OF SEQ ID NOS: 44

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
gcttcaagta gtgtgtgccc                                             20

<210> SEQ ID NO 2
<211> LENGTH: 22

```
<212> TYPE: DNA
<213> ORGANISM: Artificial Sequence
<220> FEATURE:
<223> OTHER INFORMATION: Synthetic Construct

<400> SEQUENCE: 2
ctgaagatct cggactcatt gt                                              22

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
caagcttctc tatcaaagca g                                               21

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
caagcttctc tatcaaagca g                                               21

<210> SEQ ID NO 5
<211> LENGTH: 67
<212> TYPE: DNA
<213> ORGANISM: Artificial Sequence
<220> FEATURE:
<223> OTHER INFORMATION: Synthetic Construct

<400> SEQUENCE: 5
ccatctcatc cctgcgtgtc tccgactcag ctaaggtaac ggtgatcaag cttctctatc     60
aaagcag                                                               67

<210> SEQ ID NO 6
<211> LENGTH: 67
<212> TYPE: DNA
<213> ORGANISM: Artificial Sequence
<220> FEATURE:
<223> OTHER INFORMATION: Synthetic Construct

<400> SEQUENCE: 6
ccatctcatc cctgcgtgtc tccgactcag taaggagaac ggtgatcaag cttctctatc     60
aaagcag                                                               67

<210> SEQ ID NO 7
<211> LENGTH: 67
<212> TYPE: DNA
<213> ORGANISM: Artificial Sequence
<220> FEATURE:
<223> OTHER INFORMATION: Synthetic Construct

<400> SEQUENCE: 7
ccatctcatc cctgcgtgtc tccgactcag aagaggattc ggtgatcaag cttctctatc     60
aaagcag                                                               67

<210> SEQ ID NO 8
<211> LENGTH: 67
<212> TYPE: DNA
```

<213> ORGANISM: Artificial Sequence
<220> FEATURE:
<223> OTHER INFORMATION: Synthetic Construct

<400> SEQUENCE: 8
ccatctcatc cctgcgtgtc tccgactcag taccaagatc ggtgatcaag cttctctatc    60
aaagcag                                                             67

<210> SEQ ID NO 9
<211> LENGTH: 67
<212> TYPE: DNA
<213> ORGANISM: Artificial Sequence
<220> FEATURE:
<223> OTHER INFORMATION: Synthetic Constuct

<400> SEQUENCE: 9
ccatctcatc cctgcgtgtc tccgactcag cagaaggaac ggtgatcaag cttctctatc    60
aaagcag                                                             67

<210> SEQ ID NO 10
<211> LENGTH: 67
<212> TYPE: DNA
<213> ORGANISM: Artificial Sequence
<220> FEATURE:
<223> OTHER INFORMATION: Synthetic Construct

<400> SEQUENCE: 10
ccatctcatc cctgcgtgtc tccgactcag ctgcaagttc ggtgatcaag cttctctatc    60
aaagcag                                                             67

<210> SEQ ID NO 11
<211> LENGTH: 67
<212> TYPE: DNA
<213> ORGANISM: Artificial Sequence
<220> FEATURE:
<223> OTHER INFORMATION: Synthetic Construct

<400> SEQUENCE: 11
ccatctcatc cctgcgtgtc tccgactcag ttcgtgattc ggtgatcaag cttctctatc    60
aaagcag                                                             67

<210> SEQ ID NO 12
<211> LENGTH: 67
<212> TYPE: DNA
<213> ORGANISM: Artificial Sequence
<220> FEATURE:
<223> OTHER INFORMATION: Synthetic Construct

<400> SEQUENCE: 12
ccatctcatc cctgcgtgtc tccgactcag ttccgataac ggtgatcaag cttctctatc    60
aaagcag                                                             67

<210> SEQ ID NO 13
<211> LENGTH: 67
<212> TYPE: DNA
<213> ORGANISM: Artificial Sequence
<220> FEATURE:
<223> OTHER INFORMATION: Synthetic Construct

<400> SEQUENCE: 13
ccatctcatc cctgcgtgtc tccgactcag tgagcggaac ggtgatcaag cttctctatc    60
aaagcag                                                             67

<210> SEQ ID NO 14
<211> LENGTH: 67
<212> TYPE: DNA
<213> ORGANISM: Artificial Sequence
<220> FEATURE:
<223> OTHER INFORMATION: Synthetic Construct

<400> SEQUENCE: 14
ccatctcatc cctgcgtgtc tccgactcag ctgaccgaac ggtgatcaag cttctctatc    60
aaagcag                                                              67

<210> SEQ ID NO 15
<211> LENGTH: 134
<212> TYPE: DNA
<213> ORGANISM: Artificial Sequence
<220> FEATURE:
<223> OTHER INFORMATION: Synthetic Construct

<400> SEQUENCE: 15
ccatctcatc cctgcgtgtc tccgactcag tcctcgaatc ggtgatcaag cttctctatc    60
aaagcagcca tctcatccct gcgtgtctcc gactcagtcc tcgaatcggt gatcaagctt   120
ctctatcaaa gcag                                                     134

<210> SEQ ID NO 16
<211> LENGTH: 67
<212> TYPE: DNA
<213> ORGANISM: Artificial Sequence
<220> FEATURE:
<223> OTHER INFORMATION: Synthetic Construct

<400> SEQUENCE: 16
ccatctcatc cctgcgtgtc tccgactcag taggtggttc ggtgatcaag cttctctatc    60
aaagcag                                                              67

<210> SEQ ID NO 17
<211> LENGTH: 67
<212> TYPE: DNA
<213> ORGANISM: Artificial Sequence
<220> FEATURE:
<223> OTHER INFORMATION: Synthetic Construct

<400> SEQUENCE: 17
ccatctcatc cctgcgtgtc tccgactcag tctaacggac ggtgatcaag cttctctatc    60
aaagcag                                                              67

<210> SEQ ID NO 18
<211> LENGTH: 67
<212> TYPE: DNA
<213> ORGANISM: Artificial Sequence
<220> FEATURE:
<223> OTHER INFORMATION: Synthetic Construct

<400> SEQUENCE: 18
ccatctcatc cctgcgtgtc tccgactcag ttggagtgtc ggtgatcaag cttctctatc    60
aaagcag                                                              67

<210> SEQ ID NO 19
<211> LENGTH: 67
<212> TYPE: DNA
<213> ORGANISM: Artificial Sequence
<220> FEATURE:

<223> OTHER INFORMATION: Synthetic Construct

<400> SEQUENCE: 19
ccatctcatc cctgcgtgtc tccgactcag tctagaggtc ggtgatcaag cttctctatc    60
aaagcag    67

<210> SEQ ID NO 20
<211> LENGTH: 67
<212> TYPE: DNA
<213> ORGANISM: Artificial Sequence
<220> FEATURE:
<223> OTHER INFORMATION: Synthetic Construct

<400> SEQUENCE: 20
ccatctcatc cctgcgtgtc tccgactcag tctggatgac ggtgatcaag cttctctatc    60
aaagcag    67

<210> SEQ ID NO 21
<211> LENGTH: 67
<212> TYPE: DNA
<213> ORGANISM: Artificial Sequence
<220> FEATURE:
<223> OTHER INFORMATION: Synthetic Construct

<400> SEQUENCE: 21
ccatctcatc cctgcgtgtc tccgactcag tctattcgtc ggtgatcaag cttctctatc    60
aaagcag    67

<210> SEQ ID NO 22
<211> LENGTH: 67
<212> TYPE: DNA
<213> ORGANISM: Artificial Sequence
<220> FEATURE:
<223> OTHER INFORMATION: Synthetic Construct

<400> SEQUENCE: 22
ccatctcatc cctgcgtgtc tccgactcag aggcaattgc ggtgatcaag cttctctatc    60
aaagcag    67

<210> SEQ ID NO 23
<211> LENGTH: 67
<212> TYPE: DNA
<213> ORGANISM: Artificial Sequence
<220> FEATURE:
<223> OTHER INFORMATION: Synthetic Construct

<400> SEQUENCE: 23
ccatctcatc cctgcgtgtc tccgactcag ttagtcggac ggtgatcaag cttctctatc    60
aaagcag    67

<210> SEQ ID NO 24
<211> LENGTH: 67
<212> TYPE: DNA
<213> ORGANISM: Artificial Sequence
<220> FEATURE:
<223> OTHER INFORMATION: Synthetic Construct

<400> SEQUENCE: 24
ccatctcatc cctgcgtgtc tccgactcag cagatccatc ggtgatcaag cttctctatc    60
aaagcag    67

<210> SEQ ID NO 25
<211> LENGTH: 67
<212> TYPE: DNA
<213> ORGANISM: Artificial Sequence
<220> FEATURE:
<223> OTHER INFORMATION: Synthetic Construct

<400> SEQUENCE: 25
ccatctcatc cctgcgtgtc tccgactcag tcgcaattac ggtgatcaag cttctctatc    60
aaagcag                                                              67

<210> SEQ ID NO 26
<211> LENGTH: 67
<212> TYPE: DNA
<213> ORGANISM: Artificial Sequence
<220> FEATURE:
<223> OTHER INFORMATION: Synthetic Construct

<400> SEQUENCE: 26
ccatctcatc cctgcgtgtc tccgactcag ttcgagacgc ggtgatcaag cttctctatc    60
aaagcag                                                              67

<210> SEQ ID NO 27
<211> LENGTH: 67
<212> TYPE: DNA
<213> ORGANISM: Artificial Sequence
<220> FEATURE:
<223> OTHER INFORMATION: Synthetic Construct

<400> SEQUENCE: 27
ccatctcatc cctgcgtgtc tccgactcag tgccacgaac ggtgatcaag cttctctatc    60
aaagcag                                                              67

<210> SEQ ID NO 28
<211> LENGTH: 67
<212> TYPE: DNA
<213> ORGANISM: Artificial Sequence
<220> FEATURE:
<223> OTHER INFORMATION: Synthetic Constructs

<400> SEQUENCE: 28
ccatctcatc cctgcgtgtc tccgactcag aacctcattc ggtgatcaag cttctctatc    60
aaagcag                                                              67

<210> SEQ ID NO 29
<211> LENGTH: 55
<212> TYPE: DNA
<213> ORGANISM: Artificial Sequence
<220> FEATURE:
<223> OTHER INFORMATION: Synthetic Construct

<400> SEQUENCE: 29
cctctctatg ggcagtcggt gatcctgaga tactctgatg cacaaaatag agtgg         55

<210> SEQ ID NO 30
<211> LENGTH: 55
<212> TYPE: DNA
<213> ORGANISM: Artificial Sequence
<220> FEATURE:
<223> OTHER INFORMATION: Synthetic Construct

<400> SEQUENCE: 30
cctctctatg ggcagtcggt gatttacaac ctctctgatg cacaaaatag agtgg         55

<210> SEQ ID NO 31
<211> LENGTH: 55
<212> TYPE: DNA
<213> ORGANISM: Artificial Sequence
<220> FEATURE:
<223> OTHER INFORMATION: Synthetic Construct

<400> SEQUENCE: 31
cctctctatg ggcagtcggt gataaccatc cgctctgatg cacaaaatag agtgg        55

<210> SEQ ID NO 32
<211> LENGTH: 55
<212> TYPE: DNA
<213> ORGANISM: Artificial Sequence
<220> FEATURE:
<223> OTHER INFORMATION: Synthetic Construct

<400> SEQUENCE: 32
cctctctatg ggcagtcggt gatatccgga atctctgatg cacaaaatag agtgg        55

<210> SEQ ID NO 33
<211> LENGTH: 55
<212> TYPE: DNA
<213> ORGANISM: Artificial Sequence
<220> FEATURE:
<223> OTHER INFORMATION: Synthetic Construct

<400> SEQUENCE: 33
cctctctatg ggcagtcggt gatcgaggtt atctctgatg cacaaaatag agtgg        55

<210> SEQ ID NO 34
<211> LENGTH: 55
<212> TYPE: DNA
<213> ORGANISM: Artificial Sequence
<220> FEATURE:
<223> OTHER INFORMATION: Synthetic Construct

<400> SEQUENCE: 34
cctctctatg ggcagtcggt gattccaagc tgctctgatg cacaaaatag agtgg        55

<210> SEQ ID NO 35
<211> LENGTH: 55
<212> TYPE: DNA
<213> ORGANISM: Artificial Sequence
<220> FEATURE:
<223> OTHER INFORMATION: Synthetic Construct

<400> SEQUENCE: 35
cctctctatg ggcagtcggt gattcttaca cactctgatg cacaaaatag agtgg        55

<210> SEQ ID NO 36
<211> LENGTH: 57
<212> TYPE: DNA
<213> ORGANISM: Artificial Sequence
<220> FEATURE:
<223> OTHER INFORMATION: Synthetic Construct

<400> SEQUENCE: 36
cctctctatg ggcagtcggt gatttctcat tgaactctga tgcacaaaat agagtgg      57

<210> SEQ ID NO 37
<211> LENGTH: 56
<212> TYPE: DNA
<213> ORGANISM: Artificial Sequence
<220> FEATURE:
<223> OTHER INFORMATION: Synthetic Construct

<400> SEQUENCE: 37
cctctctatg ggcagtcggt gattcgcatc gttctctgat gcacaaaata gagtgg    56

<210> SEQ ID NO 38
<211> LENGTH: 57
<212> TYPE: DNA
<213> ORGANISM: Artificial Sequence
<220> FEATURE:
<223> OTHER INFORMATION: Synthetic Construct

<400> SEQUENCE: 38
cctctctatg ggcagtcggt gattaagcca ttgtctctga tgcacaaaat agagtgg    57

<210> SEQ ID NO 39
<211> LENGTH: 56
<212> TYPE: DNA
<213> ORGANISM: Artificial Sequence
<220> FEATURE:
<223> OTHER INFORMATION: Synthetic Construct

<400> SEQUENCE: 39
cctctctatg ggcagtcggt gataaggaat cgtctctgat gcacaaaata gagtgg    56

<210> SEQ ID NO 40
<211> LENGTH: 57
<212> TYPE: DNA
<213> ORGANISM: Artificial Sequence
<220> FEATURE:
<223> OTHER INFORMATION: Synthetic Construct

<400> SEQUENCE: 40
cctctctatg ggcagtcggt gatcttgaga atgtctctga tgcacaaaat agagtgg    57

<210> SEQ ID NO 41
<211> LENGTH: 57
<212> TYPE: DNA
<213> ORGANISM: Artificial Sequence
<220> FEATURE:
<223> OTHER INFORMATION: Synthetic Construct

<400> SEQUENCE: 41
cctctctatg ggcagtcggt gattggagga cggactctga tgcacaaaat agagtgg    57

<210> SEQ ID NO 42
<211> LENGTH: 56
<212> TYPE: DNA
<213> ORGANISM: Artificial Sequence
<220> FEATURE:
<223> OTHER INFORMATION: Synthetic Construct

<400> SEQUENCE: 42
cctctctatg ggcagtcggt gattaacaat cggctctgat gcacaaaata gagtgg    56

<210> SEQ ID NO 43
<211> LENGTH: 56
<212> TYPE: DNA
<213> ORGANISM: Artificial Sequence
<220> FEATURE:
<223> OTHER INFORMATION: Synthetic Construct

<400> SEQUENCE: 43
cctctctatg ggcagtcggt gatctgacat aatctctgat gcacaaaata gagtgg    56

<210> SEQ ID NO 44

```
<211> LENGTH: 56
<212> TYPE: DNA
<213> ORGANISM: Artificial Sequence
<220> FEATURE:
<223> OTHER INFORMATION: Synthetic Construct

<400> SEQUENCE: 44
cctctctatg ggcagtcggt gatttccact tcgctctgat gcacaaaata gagtgg        56
```

METHOD OF QUANTIFYING HIV RESERVOIRS BY INDUCED TRANSCRIPTION BASED SEQUENCING

RELATED APPLICATION

This application claims priority from U.S. Provisional Application No. 62/564,098 filed Sep. 27, 2017, the subject matter of which is incorporated herein by reference in its entirety.

GOVERNMENT FUNDING

This invention was made with government support under Grant Nos. A1096113, awarded by The National Institutes of Health. The United States government has certain rights to the invention.

SEQUENCE LISTING

The instant application contains a Sequence Listing which has been submitted electronically in TXT format and is hereby incorporated by reference in its entirety. Said TXT copy, was created on Apr. 1, 2022, is named CWR024839WO ORD and is 10,666 bytes in size.

BACKGROUND

The standard method to measure the human immunodeficiency virus (HIV) reservoir is the quantitative viral outgrowth assay (Q-VOA), which amplifies replication-competent viruses released from latently infected cells in feeder cells. Unfortunately, this assay is labor intensive, semi-quantitative, and fails to detect non-induced, or poorly induced, infectious proviruses. PCR-based assays that measure total proviral and integrated DNA are technically easier to perform than Q-VOA, but their interpretation is complicated by the presence of a large excess of defective proviruses.

Recent analyses of HIV integration sites in individuals on antiretroviral treatment (ART) have shown that HIV-infected, clonally proliferating cells make up an increasing fraction, and often the majority, of the infected cell reservoir over time. These proliferating cells are likely to have HIV integration sites in genes associated with cell proliferation and cancer. Although the majority of these proliferating cells harbor defective proviruses, they can give rise to intermittent low-level viremias ("blips") during suppressive ART, and produce infectious virus. Thus, expansion of HIV-infected cells contributes significantly to the persistence of the infectious HIV reservoir (despite one report to the contrary).

PCR can also be used to measure the levels of inducible viral RNA. The levels of cell-associated HIV-1 RNA after induction strongly correlate with virion production (p=0.67, P<0.001). Discrepancies between Q-VOA and inducible RNA measurements are therefore probably due to assay inefficiencies, restrictions on viral infectivity from partially reactivated T-cells, and the presence of transcriptionally active or inducible yet defective proviruses.

The best current RNA induction assay, the Tat/Rev Induced limiting dilution assay (TILDA), measures the frequency of CD4$^+$ T-cells producing HIV multiply spliced (ms) Tat/Rev RNA upon mitogenic stimulation. HIV msRNAs (Tat/Rev) come closer to accurately reflecting active viral production since they are only produced after proviral induction. However, defective proviruses may be contributing significantly to the TILDA signal since there is a strong correlation between total proviral DNA levels and TILDA measurements. TILDA also lacks the broad dynamic range needed to easily compare the efficiencies of various latency reversing agents (LRAs).

SUMMARY

Embodiments described herein relate to methods of determining the latent HIV reservoir level in a subject. The method includes obtaining a blood sample from a HIV+ subject and isolating CD4+ T cells from the biological sample. The method also includes administering one or more HIV transcription inducing agents to the isolated CD4+ T cells and isolating RNA from the CD4+ T-cells that includes HIV env mRNA.

The method further includes producing a plurality of first amplicons from the plurality of RNA using a first primer set that corresponds to an HIV genomic region encoding the HIV env protein. The method also includes producing a plurality of second amplicons from the plurality of first amplicons using a second primer set, the second primer set including one or more adapter sequences and/or uniquely identifiable barcode sequences.

The method further includes determining the nucleic acid sequences of the second amplicons. The determined nucleic acid sequences in the sample are indicative of the amount of inducible cell-associated HIV env RNA in the sample and indicative of the latent HIV reservoir level in the subject.

Other embodiments described herein also relate to methods of determining the efficacy of latency reversal agents for reactivating latent HIV-1 reservoirs. The method includes administering one or more candidate latency reversal agents to a sample of isolated CD4+ T cells and isolating RNA from the CD4+ T-cells that includes HIV env mRNA.

The method further includes producing a plurality of first amplicons from the plurality of RNA using a first primer set that corresponds to an HIV genomic region encoding the HIV env protein. The method also includes producing a plurality of second amplicons from the plurality of first ampliconsusing a second primer set, the second primer set including one or more adapter sequences and/or uniquely identifiable barcode sequences.

The method further includes determining the nucleic acid sequences of the second amplicons. The determined nucleic acid sequences in the sample are indicative of the amount of HIV RNA+ cells in the sample and the increase in HIV RNA+ cells compared to a control is indicative of an effective latency reversal agent.

BRIEF DESCRIPTION OF THE DRAWINGS

(A) Quantitative measurement of reservoir size using EDITS. The calibration curve was produced by sorting of specific numbers of TCR-activated primary memory cells infected with an HIV GFP-reporter. TCR induced cells from 5 patients are plotted, showing the range of values obtained by EDITS from three independent determinations. (B) Comparison of reservoir sizes between females and males using the data shown in FIG. 3. The average inducible reservoir size in females was 83% of the males but was not statistically significant

FIG. 7 illustrates a list of nested primers with adapters and bar codes having SEQ ID NOs: 5-44.

DETAILED DESCRIPTION

Figure 1:
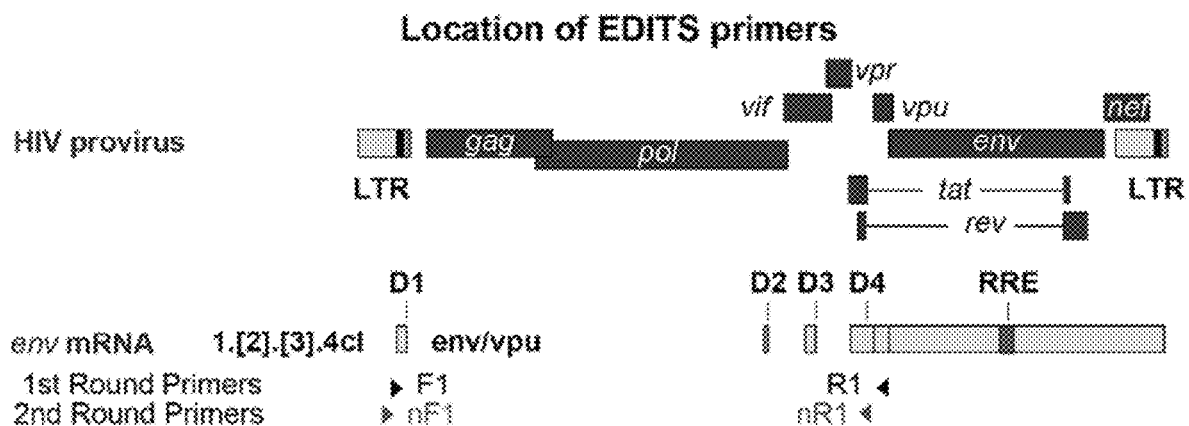
FIG. 1 illustrates design of the EDITS assay. Location of EDITS primers on the proviral HIV genome. The amplified product includes sequences from exons 1, 2, 3 and 4, spanning about 60% of the genome.
Figure 2A:
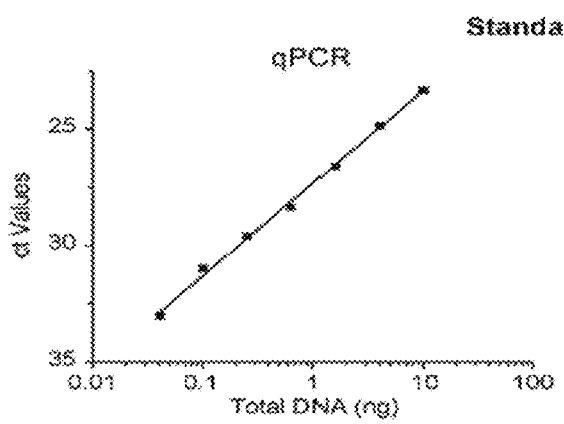
FIGS. 2(A-D) illustrate EDITS assay optimization. Comparison of standard curves obtained by qPCR (A) and multiplexed deep (Ion Torrent) sequencing (B). (C) Time course of spliced HIV env RNA induction. (D) Induction of HIV RNA from latent proviruses of well-suppressed patients after TCR stimulation. Error represents five separate assays.
Figure 2B:
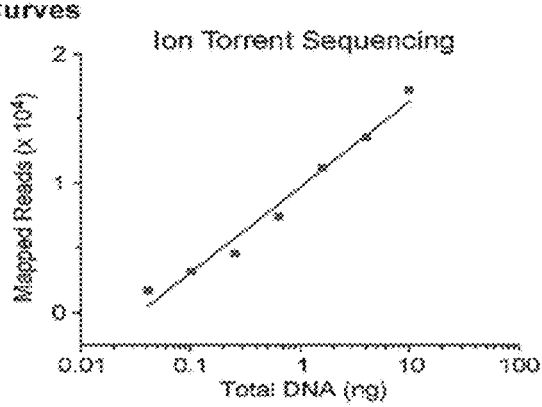
Figure 2C:
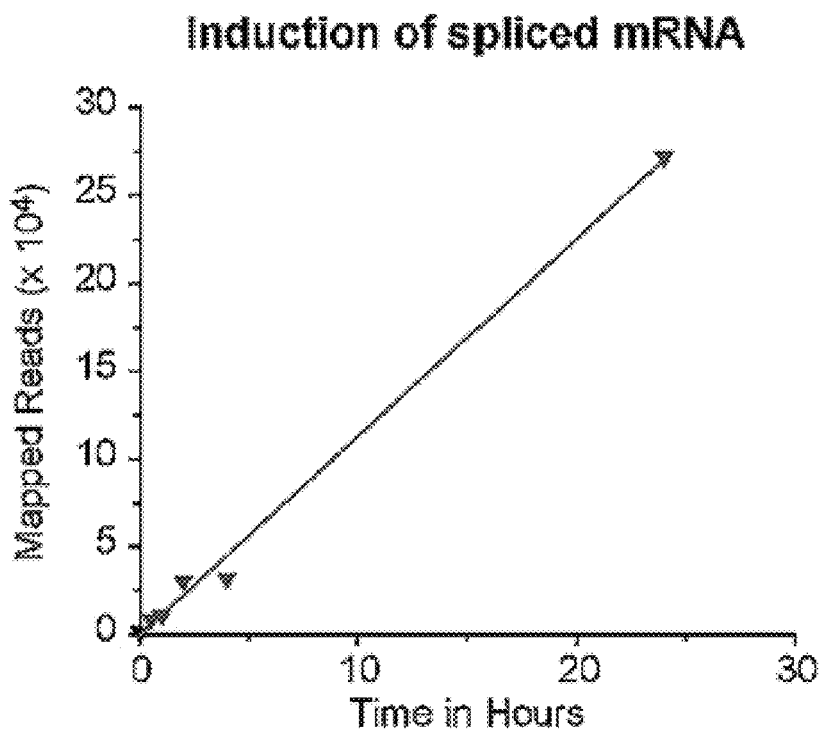
Figure 2D:
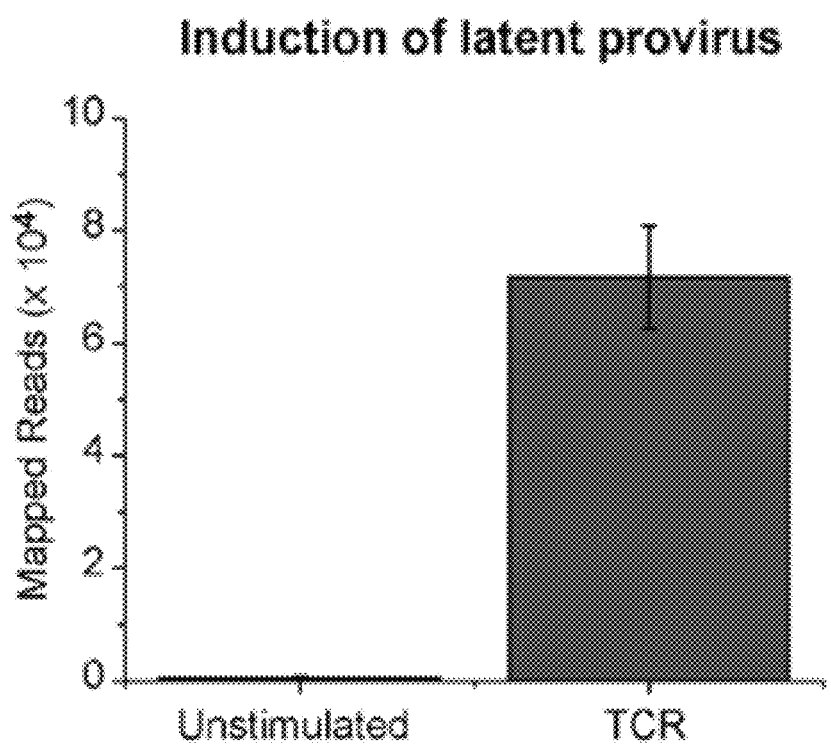

The following description of various embodiments is exemplary and explanatory only and is not to be construed as limiting or restrictive in any way. Other embodiments, features, objects, and advantages of the present teachings will be apparent from the description and accompanying drawings, and from the claims.

As used herein, "amplify", "amplifying" or "amplification reaction" and their derivatives, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ (e.g., $MgCl_2$, etc) and can also include various modifiers of ionic strength.

As used herein, "target sequence" or "target sequence of interest" and its derivatives, refers generally to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises DNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen.

As used herein, the term "primer" and its derivatives refer generally to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms "polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created that span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein. In some embodiments, the primer includes one or more cleavable groups at one or more locations within the primer.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer based polymerase that optionally can be reactivated.

The term "portion" or "region" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the nucleotides located adjacent to the 3' hydroxyl, typically the terminal 20 and even more typically the terminal 15 nucleotides. In some embodiments, the term "3' end" for example when referring to a target-specific primer, can include the terminal 10 nucleotides, the terminal 5 nucleotides, the terminal 4, 3, 2 or fewer nucleotides at the 3' end. In some embodiments, the term "3' end" when referring to a target-specific primer can include nucleotides located at nucleotide positions 10 or fewer from the 3' terminus.

As used herein, "5' end", and its derivatives, generally refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a 3' hydroxyl group, or to the 3' end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5' end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g., 3'-5' and 2'-5', inverted linkages, e.g., 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g., 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever an oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U' denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}$P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher.

As used herein, "agonist" refers to a biologically active ligand, which binds to its complementary biologically active receptor and activates the latter either to cause a biological response in the receptor or to enhance pre-existing biological activity of the receptor. "Antagonist" refers to a biologically active ligand, which binds to its complementary biologically active receptor and does not activate the latter or to cause the natural biological response in the receptor or to reduce pre-existing biological activity of the receptor. Generally, the terms "antagonist(s)" and "agonist(s)" as used herein encompasses also derivatives of said antagonist(s).

As used herein, the terms "subject," "patient," "individual," and "host" used interchangeably herein, refer to a mammal, including, but not limited to, murines, felines, simians, humans, mammalian farm animals, mammalian sport animals, and mammalian pets. The term includes mammals that are infected with as well as those that are susceptible to infection by an immunodeficiency virus. In certain embodiments, the term refers to a human infected with HIV.

As used herein, "HIV" is used herein to refer to the human immunodeficiency virus. It is recognized that the HIV virus is an example of a hyper-mutable retrovirus, having diverged into two major subtypes (HIV-1 and HIV-2), each of which has many subtypes.

As used herein, "LTR" in the context of HIV LTR means the Long Terminal Repeat, a sequence repeated at the 5' and 3' ends of the HIV genome, which consists of the enhancer and promoter regions for gene expression (U3 region), the RNA start site, and untranslated RNA sequences (RU5) such as the genomic repeat and polyadenylation sites.

As used herein, the term "viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses, e.g., HIV, is also a possible result of viral infection.

As used herein, "latency", "latent", "latently infected reservoir" or grammatical equivalents thereof refer to the integration of a viral genome or a integration of a partial viral genome within a host cell genome further characterized by (i) the undetectable level of non-spliced viral RNA (<500 copies RNA/ml by a commonly used PCR assay; Chun et al., 1997, *Proc Natl Acad Sci USA*, 94:13193-13197); (ii) absence of detectable viral production; or (iii) only about $10^5$ to $10^6$ latently infected CD4 memory T cells in a subject (Williams et al., 2004, *J Biol Chem* 279(40):42008-42017). "Latency" also means a concept describing (i) an asymptomatic clinical condition; (ii) the state of viral activity within a population of cells, or (iii) the down-regulation or absence of gene expression within an infected cell. "Latency" in the context of the viral life cycle can also refer to a virus' "lysogenic phase." In contrast, a virus is in the "lytic" phase if the viral genomes are packaged into a capsid or other viral structure, ultimately leading to lysis of the host cell and release of newly packaged viruses into the host.

As used herein, "effective amount", "effective dose", sufficient amount", "amount effective to", "therapeutically effective amount" or grammatical equivalents thereof mean a dosage sufficient to produce a desired result, to ameliorate, or in some manner, reduce a symptom or stop or reverse progression of a condition. In some embodiments, the desired result is an increase in latent HIV expression. In other embodiments, the desired result is the partial or complete eradication of a latent HIV reservoir. In an alternative embodiment, the desired result is the promotion of or the continued maintenance of HIV provirus latency. Amelioration of a symptom of a particular condition by administration of a pharmaceutical composition described herein refers to any lessening, whether permanent or temporary, lasting or transit that can be associated with the administration of the pharmaceutical composition.

As used herein, the terms "eliminating", "eradicating" or "purging" are used interchangeably.

As used herein, "latency reversing agent" or "activator of latent HIV expression" means any compound that can stimulate proviral latent DNA integrated into the genome of a host to begin transcription initiation, transcription elongation or replication and production of infectious virus and/or cell surface antigens, such as gp120 and/or gp41. Specific examples of activators of latent HIV expression are provided herein.

As used herein, "reactivated," "reactivation" or grammatical equivalents thereof, in the context of in vivo reactivated HIV, refers to an HIV that, after a period of latency, becomes transcriptionally active, and in many instances forms infectious viral particles. The term "reactivated," as used herein in the context of in vitro reactivated HIV in a subject cell, refers to an HIV (e.g., a recombinant HIV) that, after a period of latency, becomes transcriptionally active, i.e., a functional Tat protein mediates transcription from a functional HIV promoter (e.g., a long terminal repeat promoter).

As used herein, "HAART" refers to a treatment for HIV infection which is a cocktail of anti-viral drugs known as Highly Active Anti-Retroviral Therapy. Typically, HAART includes two reverse transcriptase inhibitors and a protease inhibitor.

As used herein, "HDAC inhibitor" or "inhibitor of HDAC" encompasses any synthetic, recombinant, or naturally-occurring inhibitor, including any pharmaceutical salts or hydrates of such inhibitors, and any free acids, free bases, or other free forms of such inhibitors capable of inhibiting the activity of a histone deacetylase (HDAC). "Hydroxamic acid derivative," as used herein, refers to the class of histone deacetylase inhibitors that are hydroxamic acid derivatives. Specific examples of inhibitors are provided herein.

As used herein, the term "iRNA agent," refers to small nucleic acid molecules used for RNA interference (RNAi), such as short interfering RNA (siRNA), double-stranded RNA (dsRNA), microRNA (miRNA) and short hairpin RNA (shRNA) molecules. The iRNA agents can be unmodified or chemically-modified nucleic acid molecules. The iRNA agents can be chemically synthesized or expressed from a vector or enzymatically synthesized. The use of a chemically-modified iRNA agent can improve one or more properties of an iRNA agent through increased resistance to degradation, increased specificity to target moieties, improved cellular uptake, and the like.

As used herein, the term "antisense RNA," refers to a nucleotide sequence that comprises a sequence substantially complementary to the whole or a part of an mRNA molecule and is capable of binding to the mRNA.

As used herein, the term "antibody", is defined as an immunoglobulin that has specific binding sites to combine with an antigen.

Embodiments described herein relate to methods of quantifying inducible cell-associated HIV env RNA in a biological sample. Methods described herein can measure induction of a spliced mRNA species using a nested PCR protocol that amplifies a sequence across the env splice junction. The assay methods can measure the total amount of RNA production, which reflects both changes in the frequency of induced cells and changes in the amount of induced transcription.

Embodiments described herein also relate to methods for determining latent HIV reservoir levels in a subject. In some embodiments, the HIV reservoir levels can be determined following highly active antiretroviral therapy (HAART). HAART reduces the circulating HIV to undetectable levels. Although patients adhering to the HAART regimen have minimal viremia (e.g., >20 copies of HIV/ml), HIV persists because of the existence of latent replication-competent proviruses in a very small population of resting memory CD4+ T cells.

In some embodiments, the quantification of latent HIV reservoir levels in the subject can be used to measure the efficacy of anti-retroviral therapy and/or the efficacy of latency reversal agents in reactivating latent HIV-1 reservoirs. In some embodiments, the efficacy of a candidate therapy or a combination of two or more of a candidate and/or known therapy can be determined through a method of quantification of latent HIV reservoir levels in the subject as described herein. In an exemplary embodiment, the quantification of latent HIV reservoir levels in the patient can be measured prior to a given therapy or combination of therapies and then measured again during and/or at the conclusion of a therapeutic regimen in order to determine the efficacy of a given treatment.

The methods described herein can include detecting and quantifying inducible cell-associated HIV RNA in biological samples by measuring inducible HIV envelope RNA in infected cells. The HIV envelope mRNA was chosen because the splicing pattern covers a significant portion of the proviral genome, thus minimizing readouts from defective proviruses with large deletions. The method can include generating a plurality of cDNA species from a plurality of RNA molecules in an HIV sample population administered a latency reversing agent. The assay gives minimal background signals prior to induction by latency reversal agents and is highly reproducible.

The methods described herein can be applied to a biological sample including any cell wherein an HIV genome is integrated into the cellular DNA. The cell can be a mammalian cell (e.g., a human cell). The cell can include a resting lymphoid mononuclear cell obtained from a mammal including e.g., lymphocytes, such as T cells (CD4, CD8, cytolytic, helper), B cells, natural killer cells; mononuclear phagocytes, such as monocytes, macrophages, epitheloid cells, giant cells, Kupffer cells, alveolar macrophages; dendritic cells, such as interdigitating dendrite cells, Langerhans cells, or follicular dendritic cells; granulocytes; etc. In certain embodiments, the cell is a $CD4^+$ T cell, such as a resting memory $CD4^+$ T-cell. CD4+ T-cells can be isolated from the biological sample through various well known methods. In some embodiments, $CD4^+$ memory cells are negatively isolated from PBMC purified from the biological sample using magnetic bead isolation.

Typically, a biological sample is obtained from a subject following infection with and/or diagnosis of an HIV infection in the subject. In some embodiments, the biological sample is obtained from a subject following HAART. In some embodiments, the biological sample is obtained from a subject following HIV-1 infection but prior to the subject initiating anti-retroviral treatment.

Biological samples obtained from a subject can include a tissue or body fluid samples. In certain embodiments, the sample is a blood plasma sample. In some embodiments, a blood sample can be collected from a patient and plasma samples can be processed for immediate use. Alternatively, a processed plasma sample can be stored at −80° C. for analysis at a later time.

In some embodiments, a blood sample obtained from the HIV-infected patient has a viral load ranging from about <50 to about 10,000 copies of viral RNA/ml. In certain embodiments, the subject is an aviremic subject. In some embodiments, the viral load can range from about 1000 to about 10,000 copies of viral RNA/ml. In certain embodiments, a blood sample from the HIV-infected patient has a viral load ≥1,000 copies of viral RNA/ml.

The method can include the step of administering one or more HIV transcription inducing agents to the isolated CD4+ T cells. The HIV transcription inducing agent administered to the isolated CD4+ T cells can include a latency reversing agent (LRA), a TCR activation agent (e.g., TNF-α) or a mitogen activation agent (e.g., Concanavalin A or ConA). In certain embodiments the HIV transcription inducing agent is ConA. HIV stimulation of the CD4+ T-cells with a HIV transcription inducing agent can occur for about 14 to about 24 hours. In preferred embodiments, HIV stimulation can occur for about 16 hours.

Following HIV stimulation, HIV-1 RNA can be isolated and purified from the CD4+ T-cells that include HIV env mRNA using well known methods. In an exemplary embodiment, HIV-1 RNA can be purified from using a QIAamp Viral RNA Mini Kit (Qiagen).

The methods described herein employ nucleic acid primers specifically designed to amplify HIV env RNA or its complementary DNA after memory CD4+ T-cell isolation from a blood sample of a subject and administration of a HIV transcription inducing agents, such as a latency reversing agent, to the isolated CD4+ T cells. The target sequences for the primers have been specifically selected because of their proximity to the target region, and because they exhibit a low rate of mutation that predictably enable primer hybridization and amplification of the target nucleic regions in an HIV nucleic acid population.

In some embodiments, the use of both external and nested env, specific primers (i.e., a nested PCR) can be employed to amplify an HIV-1 envelope protein coding sequence of patient derived from the HIV-1 env mRNA. In particular embodiments, the method described herein can include a two stage PCR amplification technique (i.e., producing first and second amplicons) targeted to an HIV genomic region encoding the HIV env protein. The PCR technique employed herein is not only reproducible but ensures successful amplification of samples from diverse HIV-1 subtypes while avoiding amplification of non-specific products from endogenous or any of the related viruses tested.

In some embodiments, the amplicons amplified by the two stage PCR technique can include a first and second overlapping amplicon fragments corresponding to the HIV genomic region encoding the env protein. Alternatively, it may be advantageous to produce different amplicon products using different primer combinations, such as amplicon products having a short amplicon product within the region covered by a long amplicon product where the region covered by the short product is represented in both amplicons. Both strategies provide regions with "double coverage" by the amplicons, which is beneficial in the event that one of the amplicon products fails to amplify properly.

Those of ordinary skill in the related art will also appreciate that a "nested" type amplification strategy may be employed using primers described herein. For example, nested PCR strategies are generally employed to reduce the effects of contamination typically caused by multiple primer binding sites and the generation of undesirable amplification products. In some embodiments, a first set of amplification products may be produced using a forward primer and reverse primer, which may contain some of the undesirable product. A second round of amplification using forward primers and reverse primers and the first set of amplification products may then be executed where it is unlikely that the undesirable products of the first set would have binding sites for primers of the second set resulting in a set of amplification products with much higher specificity to the desired target region.

By way of example, the HIV-1 env mRNA was amplified using a series of external and nested primers with defined cycling conditions. Primers were designed to bind to either side of the HIV env RNA splice junction at position 546-565 for Singly Spliced Forward primer F (5'-gcttcaagtagtgtgtgccc-3') (SEQ ID NO:1) and position c7609-c7630 Singly Spliced Reverse primer (5'-ctgaagatctcggactcattgt-3') (SEQ ID NO:2). Using these primers allows only the detection of late viral transcripts, eliminating any potential proviral DNA amplification. The primer binding regions are located in highly conserved regions of HIV based on the Los Alamos National Laboratory HIV Database. The nested primers were designed to bind to positions 6025-6046 (5'-caagcttctctatcaaagcag-3') (SEQ ID NO:3) and 6373-6394 (5'-tctgatgcacaaaatagagtgg-3') (SEQ ID NO:4).

The nested primers contain adapters and uniquely identifiable barcodes to facilitate the sequencing of multiple samples. Certain embodiments allow for PCR products obtained from cells treated by different latency reversal agents, and/or from different patients, to be multiplexed (i.e., barcoded, pooled and sequenced simultaneously).

Exemplary embodiments of nested primers with adapters and bar codes for use in the methods described herein are illustrated in FIG. 7. The barcode can be used to organize sequence reads into read-families, where each family derives from a single starting template molecule. A consensus sequence is derived from the reads in each group, representing the actual sequence of the initial template. By analyzing the consensus sequences, rather than each individual sequence it is possible to reduce errors from PCR since false positive variants are associated with only a fraction of the overall reads originating from the same template. Exclusion of amplification errors from read sequence analysis can increase the accuracy of allele identification and permits accurate quantitation of specific sequences allowing for identification of abundant clones in the sample and/or population.

Amplified PCR product including the second amplicons can then be purified using a commercially available clean up kit (e.g., GeneJET NGS cleanup kit (Fisher Scientific, FERK0852) to remove primers and non-amplified products and pooled for use in the next step of the method.

Methods described herein also include the step of determining the nucleic acid sequences of the amplicons. In some embodiments, the nucleic acid sequence of the amplicons can be determined using next generation sequencing methods, such as massively parallel signature sequencing (MPSS), polony sequencing, pyrosequencing, Illumina dye sequencing, SOLiD sequencing, nanopore sequencing, semiconductor sequencing (Ion Torrent), sequencing-by-ligation, sequencing-by-hybridization, RNA-Seq (Illumina), Digital Gene Expression (Helicos), and Single Molecule Sequencing by Synthesis (SMSS) (Helicos), Clonal Single Molecule Array (Solexa), shotgun sequencing, and Maxim-Gilbert sequencing. In certain embodiments, the step of determining the nucleic acid sequences of the second amplicons can include deep sequencing. In an exemplary embodiment, deep sequencing includes ion torrent semiconductor sequencing.

Typically, one or more instrument elements may be employed that automate one or more process steps. For example, embodiments of a sequencing method may be executed using instrumentation to automate and carry out some or all process steps. Embodiments of sequencing instrument employed to execute sequencing processes may include various fluidic components in the fluidic subsystem, various optical components in the optic subsystem, as well as additional components that may include microprocessor and/or microcontroller components for local control of some functions. Further, the sequencing instrument may be operatively linked to one or more external computer components, such as a computer that may for instance execute system software or firmware such as application that may provide instructional control of one or more of the components and/or some data analysis functions.

Following sequencing, the determined nucleic acid sequences can be translated into the amount of inducible cell-associated HIV env RNA in the sample and/or determine viral diversity. In an exemplary embodiment, deep sequencing reads are mapped and aligned to a subtype-specific HIV-1 reference where the number of mapped reads correspond to cell-associated HIV-1 RNA or proviral DNA.

Because latently infected cells carry only one provirus on average, the frequency of HIV env RNA reads obtained by deep sequencing is proportional to the number of inducible cells in the sample. The readouts from deep sequencing therefore can be used to estimate the total number of inducible cells in a sample by comparing them to a control.

The number of sequencing map reads can be converted to the equivalent number of cells harboring HIV-1 per $10^6$ cells by comparing the reads to an internal calibration curve. In some embodiments, the curve can be generated by cell sorting known numbers of TCR-activated primary memory CD4+ T-cells infected with a replication-competent HIV-1 virus carrying a reporter gene (i.e., green-fluorescent protein, GFP). Samples for producing the standard curve may include between 1 and 300 infected cells per well and $1.25 \times 10^6$ uninfected cells. Therefore, the curve can extend from 1 to 300 cells per well. In an exemplary embodiment, shown in FIG. 5, the calibration curve can be linear between 10 and 300 cells per sample. Additional sensitivity can be achieved using extended PCR amplifications. Thus, the methods described herein are able to provide a readout that is proportional to the number of activated cells in the peripheral circulation of a given subject or population of subjects.

In other embodiments, the amount of unique HIV RNA reads identified during sequencing can be indicative of the viral diversity in the sample. For example, the sample can include a pooled sample obtained from a particular patient population that includes a population of subjects with a high viral diversity.

Some embodiments relate to a method of determining the efficacy of an antiviral and/or latency reactivation agent in reactivating latent HIV-1 reservoirs. The method can include administering to the cells one or more antiviral and/or latency reversing agents to the isolated CD4+ cells as described herein, then quantifying the latent HIV-1 levels from the sample, and then correlating the HIV-1 levels in the sample with the efficacy of the one or more antiviral and/or latency reversing agents.

It is contemplated that the quantification of the latent HIV-1 can occur before, during, and after the course of a therapeutic regimen in order to determine the efficacy of a chosen therapeutic regimen. One way to assess the efficacy of the HIV-1 therapeutic is to compare the latent HIV-1 reactivation pre and post therapeutic administration. The amount of cell associated inducible HIV env RNA measured in the sample can then be compared to a control to determine the efficacy of the antiviral and/or LRAs. The control can be the amount of cell associated inducible HIV env RNA measured in infected cells prior to the administration of the one or more antiviral and/or latency reversing agents. In order to evaluate sex differences in CD4+ T-cells from male and female subjects, methods described herein can be modified to include an additional in vitro step allowing for the quantification of spreading viral infections in the presence of candidate agents. Therefore, in optional embodiments, purified CD4+ T-cells are stimulated with an HIV transcription inducing agent in the absence or presence of an antiretroviral agent to block spreading of HIV infection and a candidate agent. The amount of newly infected cells can be determined by measuring the increase in HIV RNA+ cells in the absence of the infection blocking agent compared to cells stimulated in the presence of the infection blocking agent.

In some embodiments the antiretroviral infection blocking agent is an integrase inhibitor (INSTI) such as raltegravir, elvitegravir and dolutegravir. In some embodiments, the candidate agent can include a selective estrogen receptor modulator (SERM). A SERM can include an ESR-1 agonist, such as 17β-estradiol or an ESR-1 antagonist, such as tamoxifen. SERMs can also include an ESR-1 coactivator agonist or antagonist as described herein.

Figure 10:
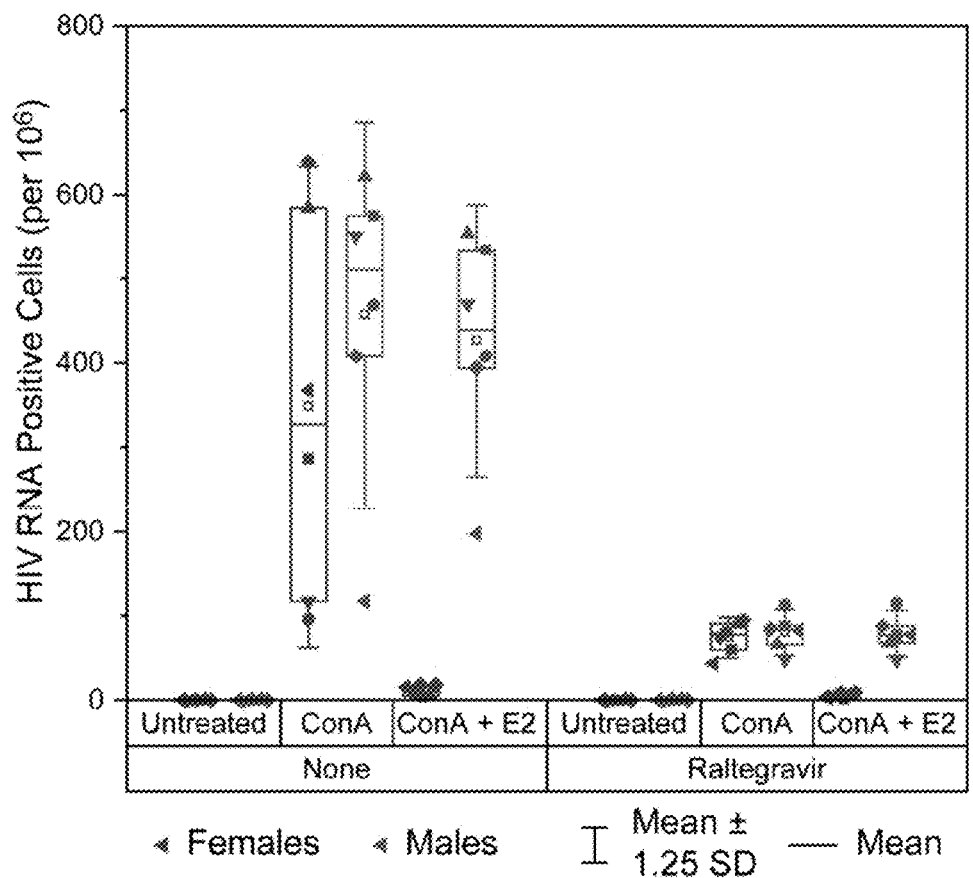
FIG. 10 illustrates estrogen blocks HIV-RNA transcription and spreading infection. Isolated CD4+ T-cells from 6 male and 6 female donors were stimulated with ConA and cultured in the presence or absence of 1 μM raltegravir with and without 300 pg/ml 17β-estradiol. The number of HIV RNA positive cells per million was quantified via EDITS after nine days of culture. Horizontal line is the mean.
Figure 11A:
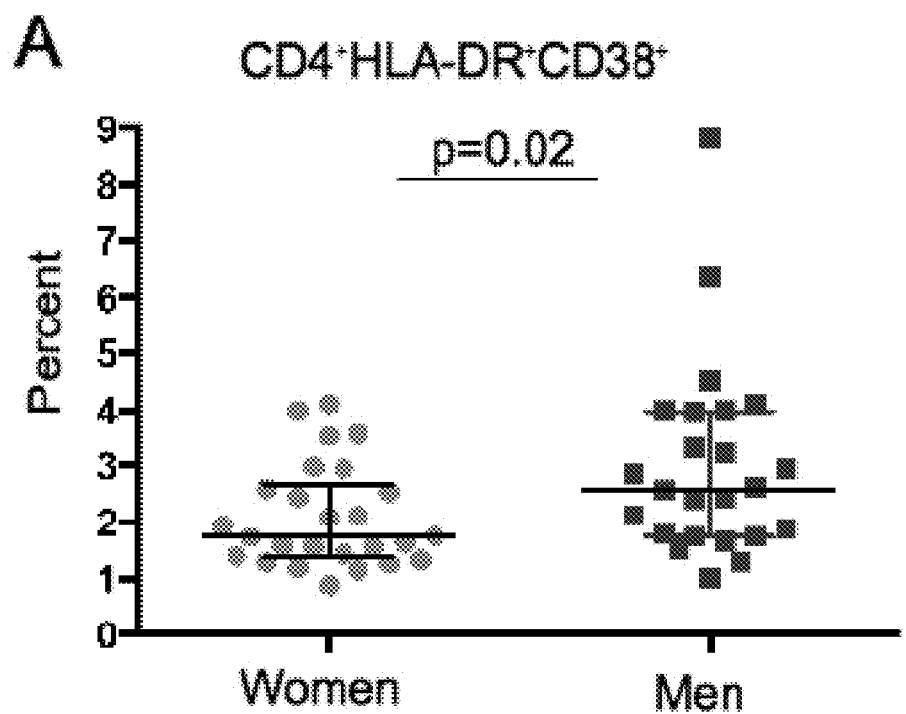
FIGS. 11A-H illustrate a comparison of activation and PD-1 expression in T-cells. Frequency of total CD4+ T-cells co-expressing (A) HLA-DR and CD38, (B) total CD4+ T-cells expressing PD-1, and (C) memory CD4+ T-cells expressing PD-1 are higher in men than in women. Total CD8+ T-cells also showed a higher frequency of (D) HLA-DR and CD38 co-expression as well as (E) PD-1 expression. A greater frequency of memory CD8+ T-cells co-expressed (F) HLA-DR and CD38 or individually expressed (G) PD-1 or (H) CCR5 in men compared to women.
Figure 11B:
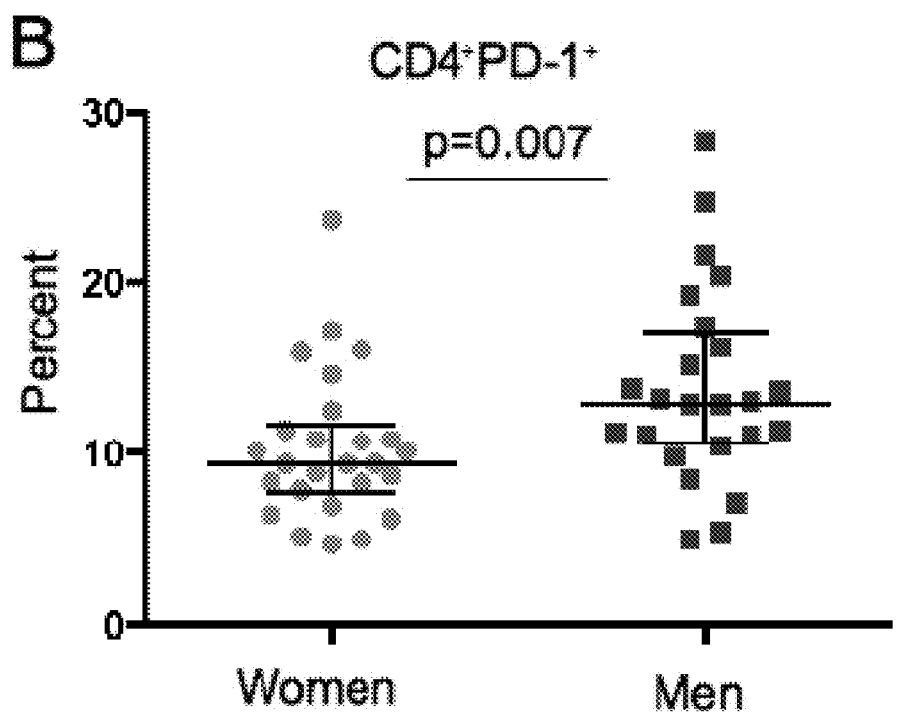
Figure 11C:
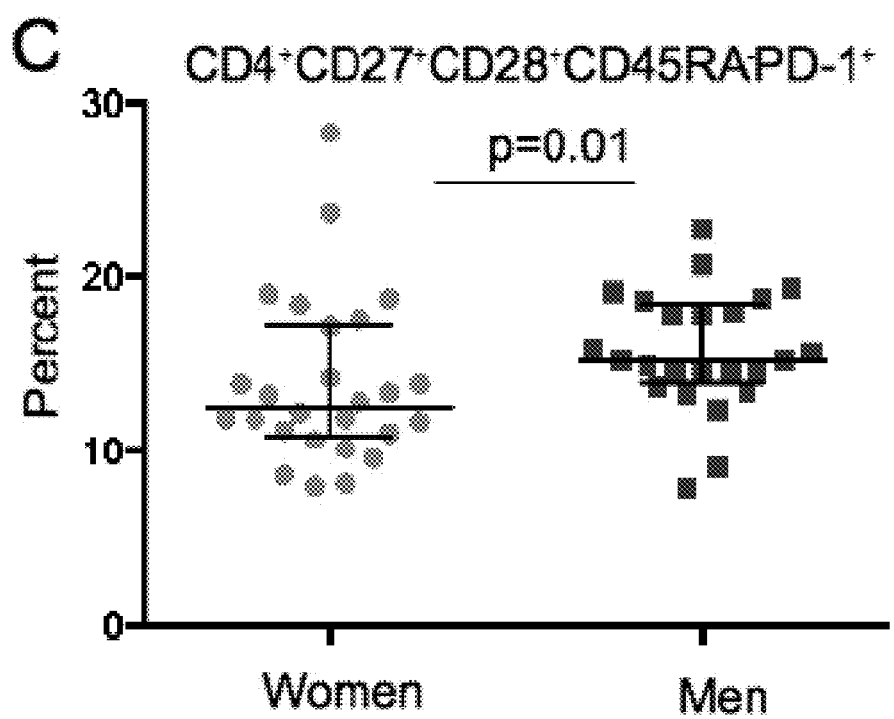
Figure 11D:
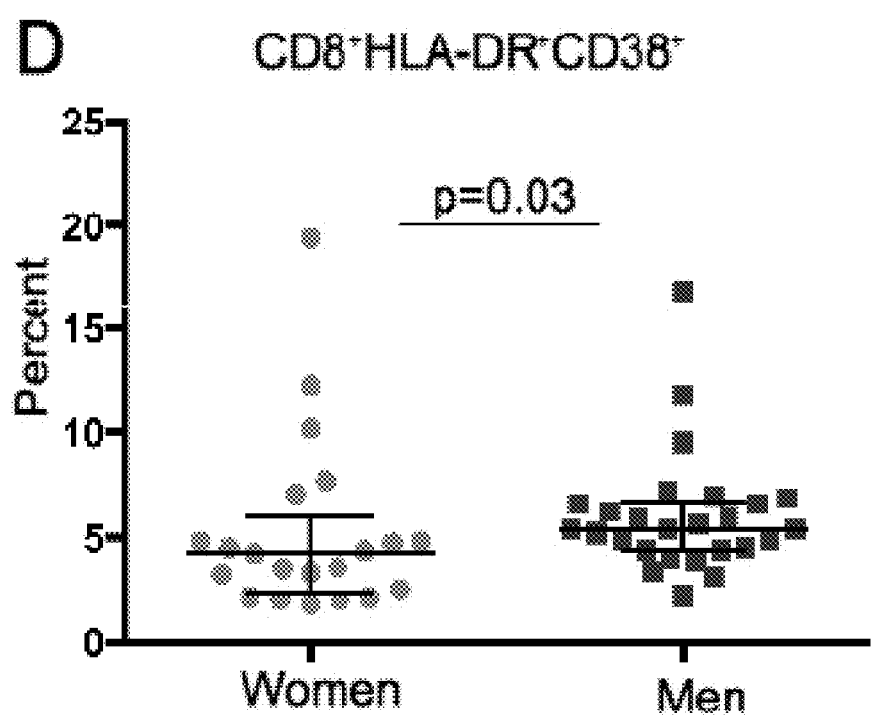
Figure 11E:
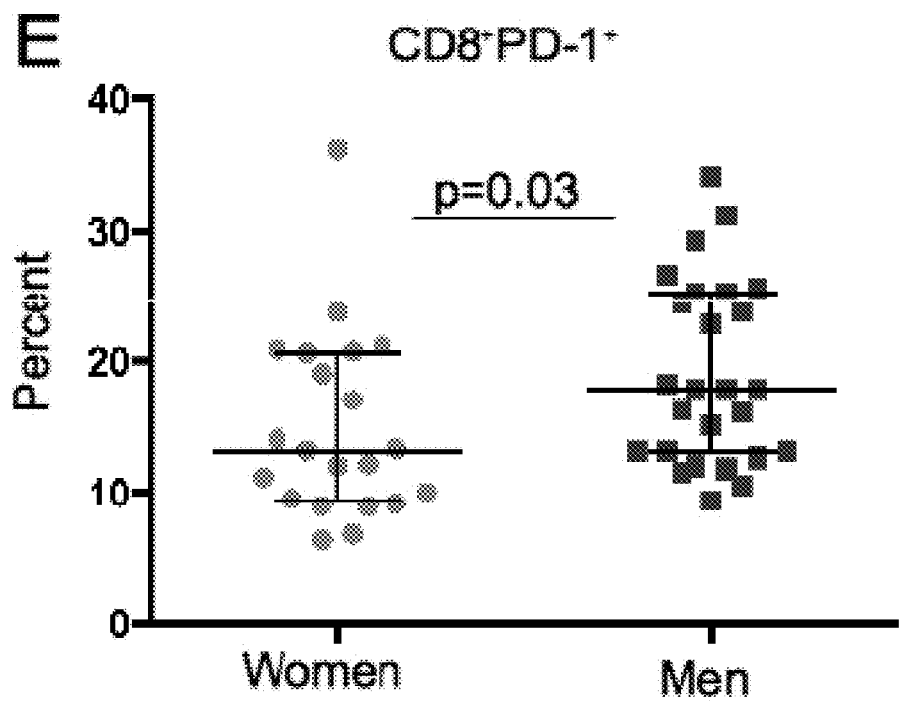
Figure 11F:
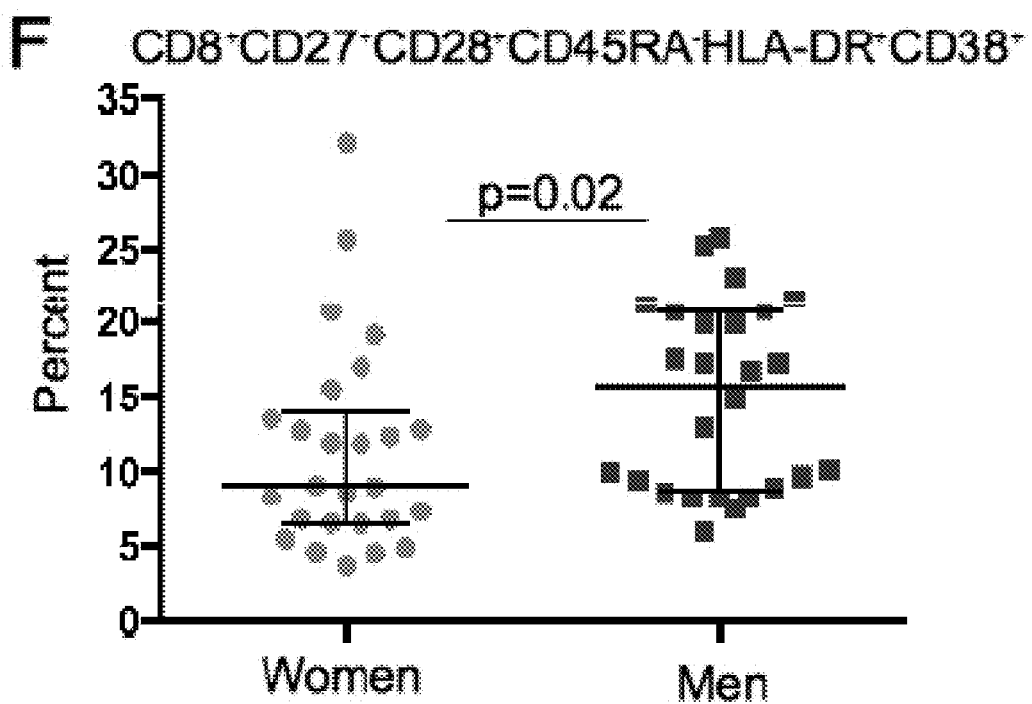
Figure 11G:
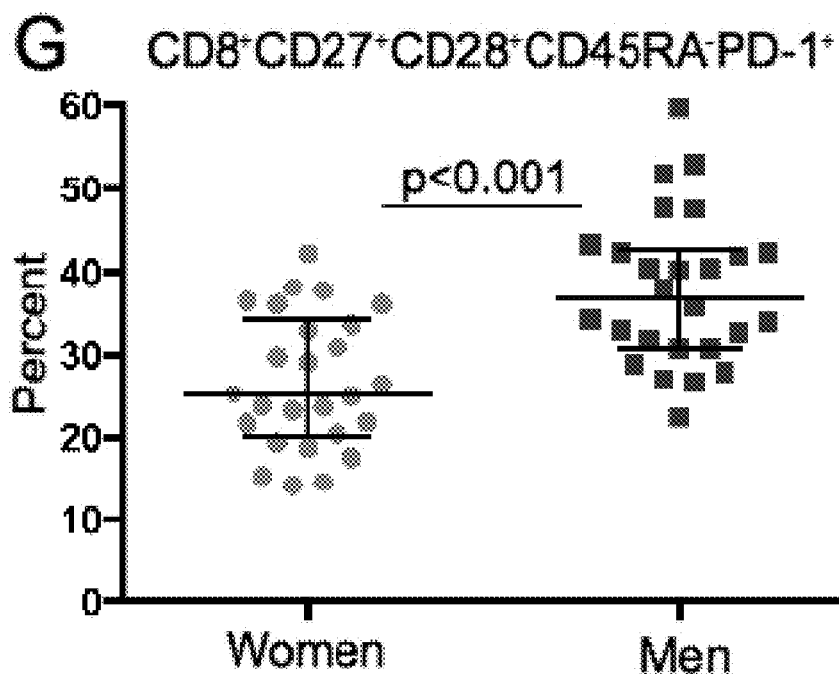
Figure 11H:
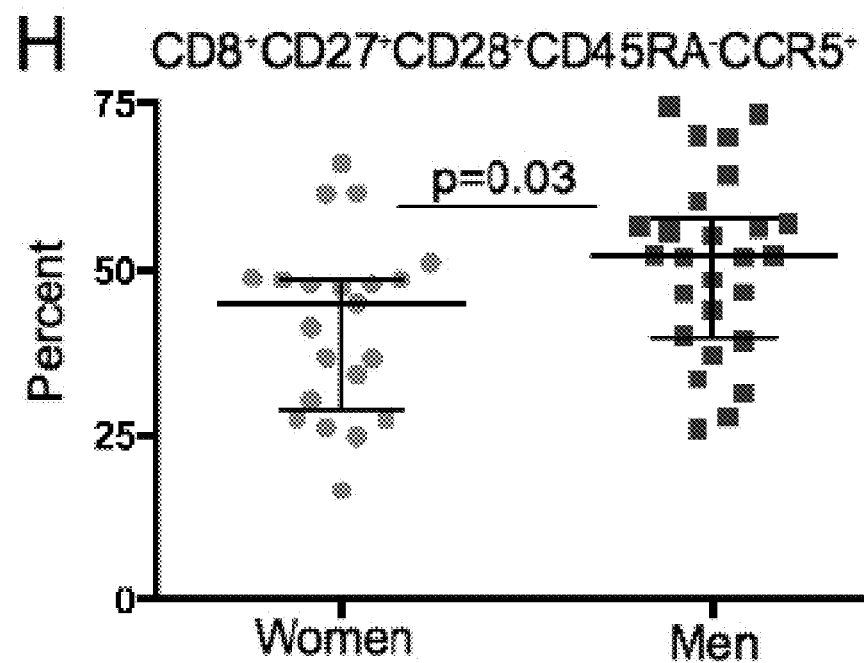
Figure 12A:
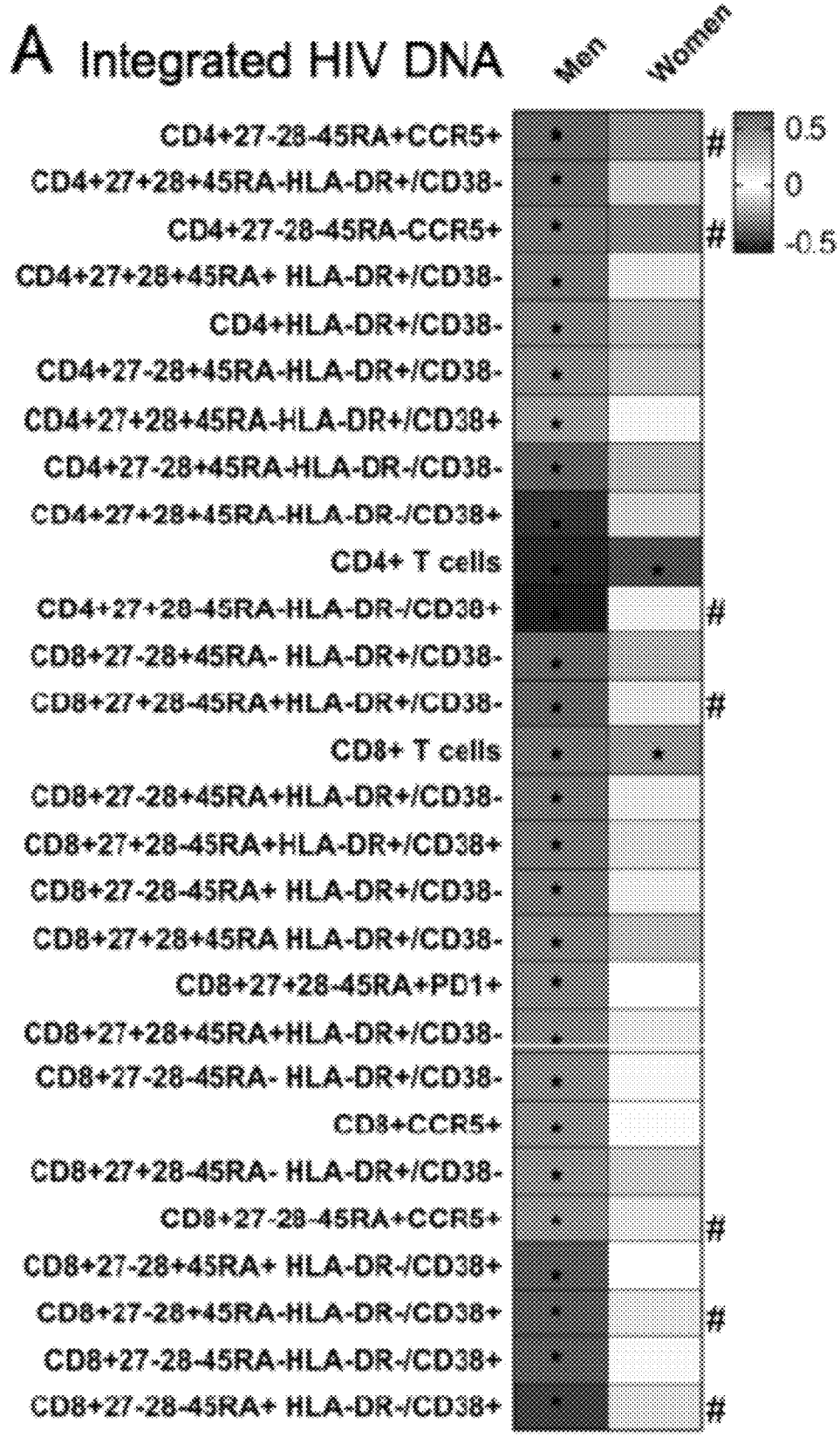
FIGS. 12A-D illustrate associations between T-cell parameters and virologic measures by sex. (A) Correlation analysis for T-cell parameters and iDNA stratified by sex: box color indicates the strength of the Spearman's correlation based on rho value, (red indicates a strong positive correlation and blue indicates a strong inverse correlation), * marks correlations with a p>0.05, # marks parameters for which there is a significant difference in correlation values between men and women. Similar information is shown for Spearman correlation analysis for T-cell parameters and HMMC gag single copy assay (B), for T-cell parameters and msRNA (C) and for T-cell parameters and usRNA (D).
Figure 12B:
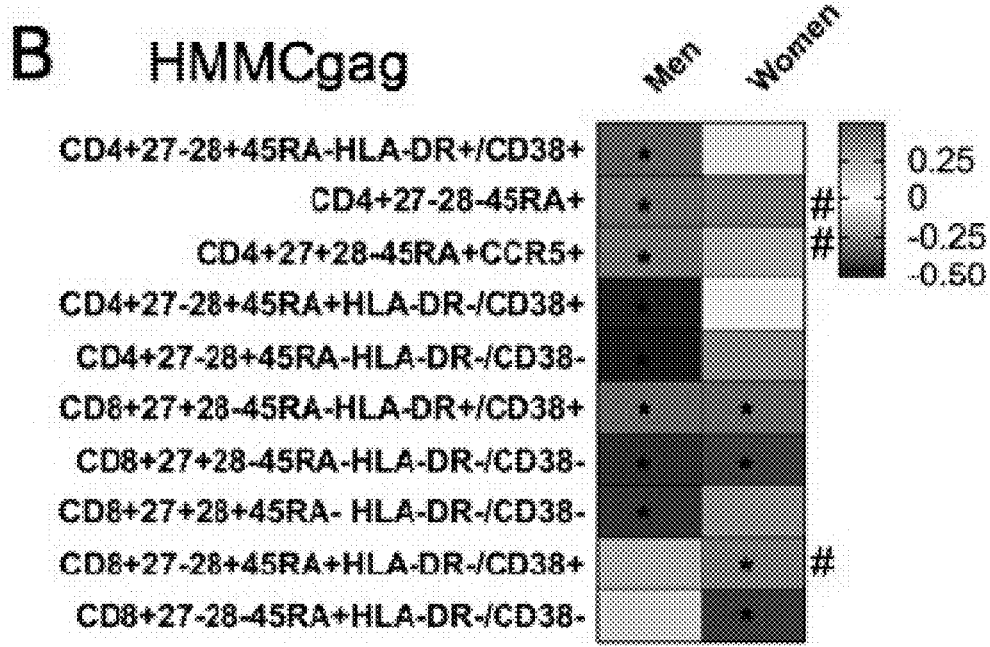
Figure 12C:
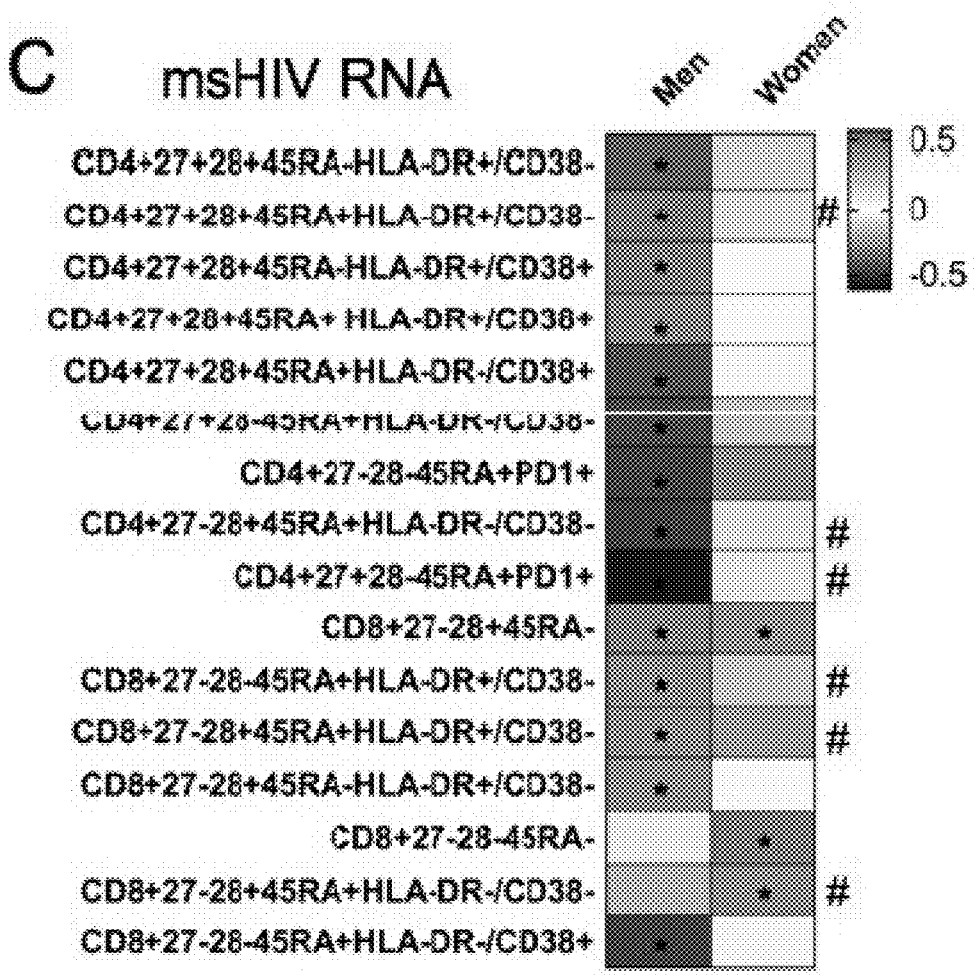
Figure 12D:
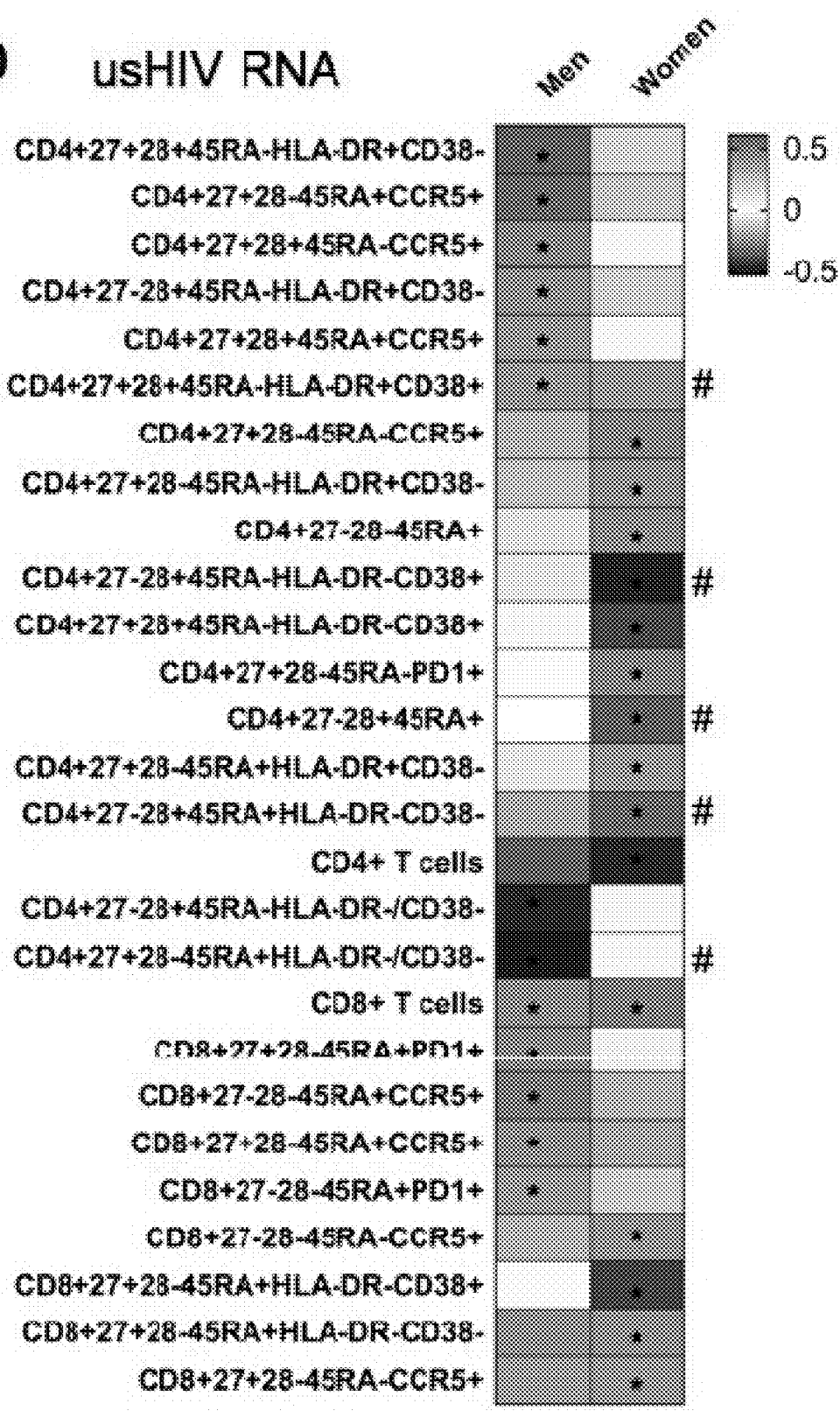

In an exemplary embodiment, as shown in FIG. 10, purified CD4+ memory cells from men and women were stimulated with the mitogen Concanavalin (Con A) in the absence or presence of 1 um Raltegravir to block spreading infection) and absence or presence of 300 pg/ml 17β-estradiol. The number of newly infected cells was determined, in accordance with the methods described herein, by measuring the HIV RNA+ cells in the absence of raltegravir after nine days. It was shown that the addition of 17β-estradiol blocked both HIV RNA induction and spreading infection in women compared to men, consistent with previous observations that the estrogen receptor-1 (ESR-1) can act as a repressor of HIV transcription.

In some embodiments, following quantification of latent HIV-1 levels from a sample obtained from the subject, a therapeutically effective amount of one or more latency reversing agents, HIV-1/AIDS drugs or antiviral agents can be administered to treat the subject with HIV-1 based on the detected HIV-1 levels.

The subject can include a host latently infected with HIV, e.g., a human latently infected with HIV. The subject can include a subject having a persistant HIV reservoir despite treatment with antiretroviral therapy (e.g., HAART). Thus, in some embodiments, the therapeutically effective amount is the amount of a pharmaceutical composition to significantly decrease a latent HIV reservoir in a latently HIV infected subject. In some embodiments, the subject can be a female, such as an HIV infected female before or during pregnancy.

It will be appreciated that one or more known latency reversing agents, HIV-1/AIDS drugs or antiviral agents may be administered to the subject with HIV-1/AIDS based on the level of HIV-1 detected. For example, in some embodiments, subjects who have high plasma HIV env RNA levels may require more aggressive HAART. For subjects with relatively low to non-measurable levels of plasma HIV RNA over prolonged periods (i.e., slow or non-progressors) may require less aggressive HAART.

It will be understood that the latency reversing agents, HIV-1/AIDS drugs or antiviral agents can be coadministered in combination with any immunomodulators, anti-infectives or vaccines. The HIV-1/AIDS antiviral agents may be used individually, sequentially, or in combination with one or more other such therapeutic agents described herein. Administration to a subject may be by the same or different route of administration or together in the same pharmaceutical formulation.

In some embodiments, the estrogen level in the subject can be determined prior to administering the latency reversing agents, HIV-1/AIDS drugs and/or antiviral agents. It has been shown that high levels of estrogen in a subject can promote HIV-1 latency. Therefore, the measured level of estrogen in a subject can be indicative to a skilled practitioner of the proper treatment of HIV-1 in the subject. For example, a subject determined to have a high level of estrogen compared to a control value can be administered a therapeutically effective amount of a latency reversing agent.

It has been shown that alteration of human estrogen receptor 1 (ESR-1) activity by the use of ESR-1 antagonists or an ESR-1 coactivator antagonist or by the use of ESR-1 agonists or an ESR-1 coactivator agonist can be used, respectively, to either promote the reactivation of latent HIV provirus in latently infected cells or limit their responses to exogenous stimuli.

Therefore, in some embodiments, the HIV-1/AIDS drugs or antiviral agents can include an ESR-1 modulating agent that modulates ESR-1 level and/or bioactivity in HIV infected cells when administered to a subject. ESR-1 modulating agents can be selected from an ESR-1 antagonist, an ESR-1 coactivator antagonist, an ESR-1 agonist and an ESR-1 coactivator agonist.

In some embodiments, the ESR-1 functional activity can be inhibited using, for example, ESR-1 antagonists and/or an ESR-1 coactivator antagonists, to induce latent HIV activity, expression, replication, and/or transcription in the HIV infected mammalian cells as well as activation or reactivation of latent provirus in the HIV infected cell. The ESR-1 and ESR-1 coactivator antagonists described herein can include any agent capable of inhibiting or decreasing the level and/or bioactivity of ESR-1 in the HIV infected cell. An agent that inhibits or reduces one or more of, the level and/or bioactivity and function of ESR-1 refers to a composition comprised of a substance that decreases and/or suppresses the biological and/or functional activity of ESR-1 to suppress HIV-1 activation and/or transcription. The biological or functional activity of ESR-1 can be suppressed, inhibited, and/or blocked in several ways including: direct inhibition of the activity of the ESR-1 (e.g., by using small molecules or peptidomimetics, dominant negative polypeptides); inhibition of genes that express the ESR-1 (e.g., by blocking the expression or activity of the genes and/or proteins); activation of genes and/or proteins that inhibit one or more of, the activity and function of ESR-1 (e.g., by increasing the expression or activity of the genes and/or proteins); inhibition of genes and/or proteins that are downstream mediators of ESR-1 (e.g., by blocking the expression and/or activity of the mediator genes and/or proteins); introduction of genes and/or proteins that negatively regulate one or more of, the activity and function of ESR-1 (e.g., by using recombinant gene expression vectors, recombinant viral vectors or recombinant polypeptides); or gene replacement with, for instance, a hypomorphic mutant of ESR-1 (e.g., by homologous recombination, over expression using recombinant gene expression or viral vectors, or mutagenesis). In certain embodiments, ESR-1 antagonists and ESR-1 coactivator antagonists described herein exhibit relatively low toxicity, permitting subjects to withstand treatment with these agents.

In some embodiments, the ESR-1 antagonists can include a selective estrogen receptor modulator (SERM), such as an selective estrogen receptor down-regulator (SERD) agent. As used herein, the term "selective estrogen receptor down-regulator" in the context of ESR-1 is an agent, which selectively binds to ESR-1 over ESRβ leading to a reduction in ESR-1 protein levels and degradation of ESR-1 in a latently infected cell and by those means prevents ESR-1 from exerting its biological actions, e.g., maintaining HIV proviral latency in the cell. In one embodiment, SERD is Fulvestrant (FASLODEX, AstraZeneca). Additional ESR-1 antagonists can include, but are not limited to, ZK-191703, SR16234, RW58668, GW5638, ICI 164,384, AZD4992, a non steroidal SERD such as CH4986399, CH4893237, diphenylfuran based compounds, and compounds from U.S. Pat. No. 7,018,994 and U.S. Pat. App. No.: 2009/0062246, the specific examples of which are incorporated herein by reference.

In other embodiments, the ESR-1 antagonist can include Tamoxifen, its active metabolites, 4-hydroxytamoxifen and/or N-desmethyl-4-hydroxytamoxifen, and/or known analogues and/or derivatives of Tamoxifen. Analogues and/or derivatives of Tamoxifen are described in, for example, U.S. Pat. Nos. 4,803,227, 5,192,525, 5,219,548, 5,446,203, 5,540,925, 5,904,930, 6,096,874, 6,172,263, 6,245,352, and 8,785,501, which are herein incorporated by reference in their entirety.

Other examples ESR-1 antagonists that can be used in the methods described herein are disclosed in U.S. Pat. Nos. 8,629,130, 8,653,072, 8,710,243, and 8,703,810, which are incorporated herein by reference in their entirety.

In an exemplary embodiment, the ESR-1 antagonist is Fluvestrant and/or Tamoxifen. In another exemplary embodiment, the ESR-1 coactivator antagonist is Gossypol. Still other ESR-1 antagonists can be identified and screened for potential induction of latent HIV activation by using a method described herein.

In other embodiments, the ESR-1 antagonist can include an agent, which reduces the expression of ESR-1 (e.g., ESR-1 iRNA agents, antisense RNA, vectors expressing iRNA agents or antisense RNA and the like). It was found that specific knock-down of the ESR-1 gene in latently infected human T-cells leads to constitutive re-activation of latent provirus (FIG. 1).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In some embodiments, ESR-1 coactivator antagonists can include agents capable of modulating the expression or activity of a molecule that influences HIV transcription via their interaction with ESR-1. Exemplary ESR-1 interacting molecules include AR, ATM, BCAR1, BRCA1, EP300, HIF1A, IGF1R, IRS1, NCOA1/SRC1, NCOA2/SRC2, NCOA3/SRC3, NRIP1, PELP1, PTPN1, RBBP8/RIM, RELA, SP1, SRC, TP53, and UIMC1. Therefore, in some embodiments, ESR-1 coactivator antagonists can include any agent capable of modulating the expression and/or activity of an ESR-1 interacting molecule 1 to influence HIV transcription via their interaction with ESR-1. In certain embodiments, the ESR-1 coactivator antagonist is Gossypol (an antagonist of the steroid receptor co-activator-3 (SRC-3/NCOA3).

It has been shown that ESR-1 antagonists and ESR-1 coactivator antagonists can sensitize latently infected cells to sub-optimum dose concentrations of proviral activators. Accordingly, in some embodiments ESR-1 antagonists and/or ESR-1 coactivator antagonists can be administered in combination with activators of latent HIV expression to synergistically enhance reactivation of latently infected cell populations of cells compared to either agent alone.

In these embodiments, the ESR-1 antagonists and/or ESR-1 coactivator antagonists can be provided in a composition that can also include a latency reversing agent that is not an ESR-1 antagonists and/or ESR-1 coactivator. Several latency reversing agents that activate latent HIV expression can be used in the methods described herein. For example, a latency reversing agent can include, but is not limited to, histone deacetylase (HDAC) inhibitors, protein kinase C agonists, and TNF-α. In certain embodiments, the latency reversing agent is selected from TNF-α and SAHA (Vorinostat).

It has been demonstrated that HDAC inhibitors induce the transcriptional activation of the HIV-1 promoter. An HDAC inhibitor can be any molecule that effects a reduction in the activity of a histone deacetylase. This includes proteins, peptides, DNA molecules (including antisense), RNA molecules (including iRNA agents and antisense) and small molecules. In some embodiments of the present invention, a HDAC inhibitor is a small interfering RNA (siRNA), for example, a si/shRNA directed against HDAC1, 2, 3, 4, 5, 6, 7, 8, 9, 10, or 11. Non-limiting examples of such HDAC inhibitors are set forth below. It is understood that HDAC inhibitors include any salts, crystal structures, amorphous structures, hydrates, derivatives, metabolites, stereoisomers, structural isomers, and prodrugs of the HDAC inhibitors described herein.

In some embodiments, an HDAC inhibitor can include short-chain fatty acids (e.g., Sodium Butyrate, Isovalerate, Valerate, 4-Phenylbutyrate (4-PBA), Phenylbutyrate (PB), Propionate, Butyramide, Isobutyramide, Phenylacetate, 3-Bromopropionate, Tributyrin, Valproic acid (Vpa), Valproate, Valproate semisodium and pivaloyloxymethyl butyrate (PIVANEX)).

In other embodiments, an HDAC inhibitor can include a hydroxamic acid derivative (e.g., suberoylanilide hydroxamic acid (SAHA, vorinostat), Trichostatin analogs such as Trichostatin A (TSA) and Trichostatin C, m-Carboxycinnamic acid bishydroxamide (CBHA), Pyroxamide, Salicylbishydroxamic acid, Suberoyl bishydroxamic acid (SBHA), Azelaic bishydroxamic acid (ABHA) Azelaic-1-hydroxamate-9-anilide (AAHA), 6-(3-Chlorophenylureido) carpoic hydroxamic acid (3Cl-UCHA), Oxamflatin [(2E)-5-[3-[(phenylsulfonyl) amino]phenyl]-pent-2-en-4-ynohydroxamic acid], A-161906 Scriptaid, PXD-101 (Prolifix), LAQ-824, CHAP, MW2796, MW2996; or any of the hydroxamic acids disclosed in U.S. Pat. Nos. 5,369,108, 5,932,616, 5,700,811, 6,087,367, and 6,511,990). In certain embodiments, the HDAC inhibitor is SAHA.

In still other embodiments, an HDAC inhibitor can include benzamide derivatives (e.g., CI-994; MS-275 [N-(2-aminophenyl)-4[N-(pyridin-3-yl methoxycarbonyl)aminomethyl]benzamide] and 3'-amino derivative of MS-275).

In yet other embodiments, an HDAC inhibitor can include cyclic peptides (e.g., Trapoxin A (TPX)-cyclic tetrapeptide (cyclo-(L-phenylalanyl-L-phenylalanyl-D-pipecolinyl-L-2-amino-8-oxo-9,10-epoxy decanoyl)), FR901228 (FK 228, depsipeptide), FR225497 cyclic tetrapeptide, Apicidin cyclic tetrapeptide [cyclo(N-O-methyl-L-tryptophanyl-L-isoleucinyl-D-pipecolinyl-L-2-amino-8-oxodecanoyl)], Apicidin Ia, Apicidin Ib, Apicidin Ic, Apicidin IIa, and Apicidin IIb, CHAP, HC-toxin cyclic tetrapeptide, WF27082 cyclic tetrapeptide, and Chlamydocin.

Additional HDAC inhibitors can include natural products, such as psammaplins and Depudecin, Electrophilic ketone derivatives such as Trifluoromethyl ketones, α-keto amides such as N-methyl-α-ketoamides, LSD1 polypeptide, TNF-alpha (TNFα), an inducible transcription factor NF-AT (nuclear factor of activated T cells), and Anti-IκBα or IκBε agents.

Protein kinase C (PKC) agonists can include non-tumor-promoting phorbol deoxyphorbol esters such as prostratin, the structural or functional analogs thereof described in US20120101283 A1, 12-deoxyphorbol 13-phenylacetate (DPP), Ingenol mebutate (ingenol-3-angelate, tradename PICATO) and bryostatins such as bryostatin-1.

It is expected that one or more activators of latent HIV expression, alone or in combination with another HIV-1/AIDS drugs or antiviral agents can purge the latent HIV from a subject's body since harboring cells with reactivated HIV can be recognized by specific CTLs (cytotoxic CD8+ T cells), by NK (Natural Killer) cells and by specific cytotoxic antibodies. The latent HIV from a subject's body can also be purged by targeting and neutralizing the reactivated HIV-1 using anti-retroviral therapy, e.g., HAART.

Another therapeutic agent useful in the treatment of HIV infection can include a component used for HAART or immunotoxins.

It will be understood that the scope of combinations of the compounds of this invention with HIV/AIDS antivirals, immunomodulators, anti-infectives or vaccines is not limited to the following list, and includes in principle any combination with any pharmaceutical composition useful for the treatment of AIDS. The HIV/AIDS antivirals and other agents will typically be employed in these combinations in their conventional dosage ranges and regimens as reported in the art.

Examples of antiviral agents include (but not restricted) ANTIVIRALS Manufacturer (Tradename and/or Drug Name Location) Indication (Activity): abacavir GlaxoSmithKline HIV infection, AIDS, ARC GW 1592 (ZIAGEN) (nRTI); 1592U89 abacavir+GlaxoSmithKline HIV infection, AIDS, ARC (nnRTI); lamivudine+(TRIZIVIR) zidovudine acemannan Carrington Labs ARC (Irving, Ill.) ACH 126443 Achillion Pharm. HIV infections, AIDS, ARC (nucleoside reverse transcriptase inhibitor); acyclovir Burroughs Wellcome HIV infection, AIDS, ARC, in combination with AZT AD-439 Tanox Biosystems HIV infection, AIDS, ARC AD-519 Tanox Biosystems HIV infection, AIDS, ARC adefovir dipivoxil Gilead HIV infection, AIDS, ARC GS 840 (RTI); AL-721 Ethigen ARC, PGL, HIV positive, (Los Angeles, Calif.), AIDS alpha interferon GlaxoSmithKline Kaposi's sarcoma, HIV, in combination w/Retrovir AMD3100 AnorMed HIV infection, AIDS, ARC (CXCR4 antagonist); amprenavir GlaxoSmithKline HIV infection, AIDS, 141 W94 (AGENERASE) ARC (PI); GW 141 VX478 (Vertex) ansamycin Adria Laboratories ARC LM 427 (Dublin, Ohio) Erbamont (Stamford, Conn.) antibody which neutralizes; Advanced Biotherapy AIDS, ARC pH labile alpha aberrant Concepts (Rockville, Interferon Md.) AR177 Aronex Pharm HIV infection, AIDS, ARC atazanavir (BMS 232632) Bristol-Myers-Squibb HIV infection, AIDS, ARC (ZRIVADA) (PI); beta-fluoro-ddA Nat'l Cancer Institute AIDS-associated diseases BMS-232623 Bristol-Myers Squibb/HIV infection, AIDS, (CGP-73547) Novartis ARC (PI); BMS-234475 Bristol-Myers Squibb/ HIV infection, AIDS, (CGP-61755) Novartis ARC (PI); capravirine Pfizer HIV infection, AIDS, (AG-1549, S-1153) ARC (nnRTI); CI-1012 Warner-Lambert HIV-1 infection cidofovir Gilead Science CMV retinitis, herpes, papillomavirus curdlan sulfate AJI Pharma USA HIV infection cytomegalovirus immune MedImmune CMV retinitis globin cytovene Syntex sight threatening CMV ganciclovir peripheral CMV retinitis delavirdine Pharmacia-Upjohn HIV infection, AIDS, (RESCRIPTOR) ARC (nnRTI); dextran Sulfate Ueno Fine Chem. Ind. AIDS, ARC, HIV Ltd. (Osaka, Japan) positive asymptomatic ddC Hoffman-La Roche HIV infection, AIDS, ARC (zalcitabine, (HMD) (nRTI); dideoxycytidine ddI Bristol-Myers Squibb HIV infection, AIDS, ARC; Dideoxyinosine (VIDEX) combination with AZT/d4T (nRTI) DPC 681 & DPC 684 DuPont HIV infection, AIDS, ARC (PI) DPC 961 & DPC 083 DuPont HIV infection AIDS, ARC (nnRTRI); emvirine Triangle Pharmaceuticals HIV infection, AIDS, ARC (CO-ACTINON) (non-nucleoside reverse transcriptase inhibitor); EL10 Elan Corp, PLC HIV infection (Gainesville, Ga.) efavirenz DuPont HIV infection, AIDS, (DMP 266) (SUSTIVA) ARC (nnRTI); Merck (STOCRIN) famciclovir Smith Kline herpes zoster, herpes simplex emtricitabine Triangle Pharmaceuticals HIV infection, AIDS, ARC FTC (CO-VIRACIL) (nRTI); Emory University emvirine Triangle Pharmaceuticals HIV infection, AIDS, ARC (COACTI-NON) (non-nucleoside reverse transcriptase inhibitor); HBY097 Hoechst Marion Roussel HIV infection, AIDS, ARC (nnRTI); hypericin VIMRx Pharm. HIV infection, AIDS, ARC recombinant human; Triton Biosciences AIDS, Kaposi's sarcoma, interferon beta (Almeda, Calif.); ARC interferon alfa-n3 Interferon Sciences ARC, AIDS indinavir; Merck (CRIXIVAN) HIV infection, AIDS, ARC, asymptomatic HIV positive, also in combination with AZT/ddI/ ddC (PI); ISIS 2922 ISIS Pharmaceuticals CMV retinitis JE2147/AG1776; Agouron HIV infection, AIDS, ARC (PI); KNI-272 Nat'l Cancer Institute HIV-assoc. diseases lamivudine; 3TC Glaxo Wellcome HIV infection, AIDS, (EPIVIR) ARC; also with AZT (nRTI); lobucavir Bristol-Myers Squibb CMV infection; lopinavir (ABT-378) Abbott HIV infection, AIDS, ARC (PI); lopinavir+ritonavir Abbott (KALETRA) HIV infection, AIDS, ARC (ABT-378/r) (PI); mozenavir AVID (Camden, N.J.) HIV infection, AIDS, ARC (DMP-450) (PI); nelfinavir Agouron HIV infection, AIDS, (VIRACEPT) ARC (PI); nevirapine Boeheringer HIV infection, AIDS, Ingleheim ARC (nnRTI); (VIRAMUNE) novapren Novaferon Labs, Inc. HIV inhibitor (Akron, Ohio); pentafusaide Trimeris HIV infection, AIDS, ARC T-20 (fusion inhibitor); peptide T Peninsula Labs AIDS octapeptide (Belmont, Calif.) sequence PRO 542 Progenics HIV infection, AIDS, ARC (attachment inhibitor); PRO 140 Progenics HIV infection, AIDS, ARC (CCR5 co-receptor inhibitor); trisodium Astra Pharm. Products, CMV retinitis, HIV infection, phosphonoformate Inc other CMV infections; PNU-140690 Pharmacia Upjohn HIV infection, AIDS, ARC (PI); probucol Vyrex HIV infection, AIDS; RBC-CD4Sheffield Med. Tech HIV infection, AIDS, (Houston Tex.) ARC; ritonavir Abbott HIV infection, AIDS, (ABT-538) (RITONAVIR) ARC (PI); saquinavir Hoffmann-LaRoche HIV infection, AIDS, (FORTOVASE) ARC (PI); stavudine d4T Bristol-Myers Squibb HIV infection, AIDS, ARC didehydrodeoxy-(ZERIT.) (nRTI); thymidine T-1249 Trimeris HIV infection, AIDS, ARC (fusion inhibitor); TAK-779 Takeda HIV infection, AIDS, ARC (injectable CCR5 receptor antagonist); tenofovir Gilead (VIREAD) HIV infection, AIDS, ARC (nRTI); tipranavir (PNU-140690) Boehringer Ingelheim HIV infection, AIDS, ARC (PI); TMC-120 & TMC-125 Tibotec HIV infections, AIDS, ARC (nnRTI); TMC-126 Tibotec HIV infection, AIDS, ARC (PI); valaciclovir GlaxoSmithKline genital HSV & CMV infections virazole Viratek/ICN (Costa asymptomatic HIV positive, ribavirin Mesa, Calif.) LAS, ARC; zidovudine; AZT GlaxoSmithKline HIV infection, AIDS, ARC, (RETROVIR) Kaposi's sarcoma in combination with other therapies (nRTI); [PI=protease inhibitor nnRTI=non-nucleoside reverse transcriptase inhibitor NRTI=nucleoside reverse transcriptase inhibitor].

According to this embodiment, a composition comprising an ESR-1 antagonist and an activator of latent HIV expression may be coadministered with any HAART regimen or component thereof. The current standard of care using HAART is usually a combination of at least three nucleoside reverse transcriptase inhibitors and frequently includes a protease inhibitor, or alternatively a non-nucleoside reverse transcriptase inhibitor.

Thus, in some embodiments, a therapeutically effective amount of a pharmaceutical composition comprising an ESR-1 or ESR-1 coactivator antagonist and an activator of latent HIV expression may be coadministered with a "cocktail" of nucleoside reverse transcriptase inhibitors, non-nucleoside HIV reverse transcriptase inhibitors, and protease inhibitors can be administered to treat a subject with HIV-1 based on the detected HIV-1 levels. For example, a pharmaceutical composition including an ESR-1 antagonist and an HDAC inhibitor may be coadministered with a cocktail of two nucleoside reverse transcriptase inhibitors (e.g., ZIDOVUDINE (AZT) and LAMIVUDINE (3TC)), and one protease inhibitor (e.g., INDINAVIR (MK-639)). A pharmaceutical composition including an ESR-1 or ESR-1 coactivator antagonist and an activator of latent HIV expression, such as an HDAC inhibitor, may also be coadministered with a cocktail of one nucleoside reverse transcriptase inhibitor (e.g., STAVUDINE (d4T)), one non-nucleoside reverse transcriptase inhibitor (e.g., NEVIRAPINE (BI-RG-587)), and one protease inhibitor (e.g., NELFINAVIR (AG-1343)). Alternatively, a composition comprising an activator of latent HIV expression and an HDAC inhibitor may be coadministered with a cocktail of one nucleoside reverse transcriptase inhibitor (e.g., ZIDOVUDINE (AZT)), and two protease inhibitors (e.g., NELFINAVIR (AG-1343) and SAQINAVIR (Ro-31-8959)).

Coadministration in the context of this invention is defined to mean the administration of more than one therapeutic agent in the course of a coordinated treatment to achieve an improved clinical outcome. Such coadministration may also be coextensive, that is, occurring during overlapping periods of time.

This regimen may be continued for a period past the point when the levels of integrated and unintegrated HIV in active and memory T cells are undetectably low. At the end of the period, the subject is weaned from HAART and from the ESR-1 antagonist and activators of latent HIV expression. At this point, the subject is monitored for reestablishment of normal immune function and for signs of reemergence of HIV infection. Additionally, any needed conjunctive immunotherapy, such as bone marrow transplants, various cytokines or vaccination, may be administered. After this, the subject is monitored on a routine basis for life to detect reemergence of HIV infection, in which case repeat therapy according to the above embodiments may be performed.

Additionally, immunotoxins may be employed in a method of the present invention. In some embodiments, an immunotoxin can be coadministered to a subject with an ESR-1 antagonist or ESR-1 coactivator antagonist and activators of latent HIV expression. An exemplary immunotoxin is an immunotoxin targeted to an HIV protein expressed on the exterior of cells, such as the viral envelope glycoprotein or a portion thereof. The term "immunotoxin" refers to a covalent or non-covalent linkage of a toxin to an antibody, such as an anti HIV envelope glycoprotein antibody. The toxin may be linked directly to the antibody, or indirectly through, for example, a linker molecule. The toxin can be selected from the group consisting of ricin-A and abrin-A.

Other embodiments described herein relate to treating HIV in a subject by inhibiting HIV reactivation in latently infected CD4+ T-cells of a subject following quantification of latent HIV-1 levels from a sample obtained from the subject. In accordance with this aspect, a method of treating HIV infection in a subject can include administering to the subject a therapeutically effective amount of a pharmaceutical composition including an ESR-1 agonist or an ESR-1 coactivator agonist. The therapeutically effective amount is an amount effective to inhibit HIV transcription in the subject's latently infected T-cells. In some embodiments, the ESR-1 agonist or ESR-1 coactivator agonist is an agonist in T-cells.

ESR-1 agonists can include a subtype-selective estrogen receptor agonist that displays selectivity for ESR-1 (ESRα) over ESRβ. Suitable Subtype-selective estrogen receptor agonists include propylpyrazole triol (PPT) (4,4',4"-(4-Propyl-[1H]-pyrazole-1,3,5-triyl)trisphenol), SKF-82958 or a compound based on a triphenylfuran-scaffold. Mixed agonists having selectivity for ERα for use in the present invention can include triarylpyrazoles or etrahydroisoquinolines. In an exemplary embodiment illustrated in FIG. 8, the ESR-1 agonist is PPT.

ESR-1 coactivator agonists can include agents capable of modulating the expression or activity of a molecule that negatively influences HIV transcription and/or represses reactivation of latent HIV expression via their interaction with ESR-1. Examples of ESR-1 interacting molecules include AR, ATM, BCAR1, BRCA1, EP300, HIF1A, IGF1R, IRS1, NCOA1/SRC1, NCOA2/SRC2, NCOA3/SRC3, NRIP1, PELP1, PTPN1, RBBP8/RIM, RELA, SP1, SRC, TP53, and UIMC1. Therefore, in some embodiments, ESR-1 coactivator agonists can include any agent capable of modulating the expression and/or activity of an ESR-1 interacting molecule compound and that negatively influences HIV transcription and/or represses reactivation of latent HIV expression via their interaction with ESR-1. In some embodiments, the ESR-1 coactivator agonist is a NCOA3/SRC3 agonist.

In some embodiments, the pharmaceutical compositions administered described herein to treat the subject with HIV-1 based on the detected HIV-1 levels can be formulated by standard techniques using one or more physiologically acceptable carriers or excipients. Suitable pharmaceutical carriers are described herein and in "Remington's Pharmaceutical Sciences" by E. W. Martin. The latency reversing agents, HIV-1/AIDS drugs and/or antiviral agents described herein can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablets or a capsule prepared by conventional means with a pharmaceutically acceptable excipient. Preferred are tablets and gelatin capsules comprising the active ingredient, i.e., a small molecule compound of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The compositions described herein can also be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compounds can also be formulated in rectal compositions, for example, suppositories or retention enemas, for example, containing conventional suppository bases, for example, cocoa butter or other glycerides.

Furthermore, the latency reversing agents, HIV-1/AIDS drugs and/or antiviral agents described herein can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

The dosage of active compounds administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of one or more active compound for the treatment of HIV described herein is a dosage that is sufficient to achieve the desired effect. Optimal dosing schedules can be calculated from measurements of compound accumulation in the body of a subject. In general, dosage may be given once or more daily, weekly, or monthly. Persons of ordinary skill in the art can easily determine optimum dosages, dosing methodologies and repetition rates.

In another embodiment, a pharmaceutical composition including a latency reversing agents, HIV-1/AIDS drugs and/or antiviral agents described can be administered in a daily dose in the range from about 0.1 mg of each compound per kg of subject weight (0.1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In yet another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, latency reversing agents, HIV-1/AIDS drugs and/or antiviral agents, and/or ESR-1 modulating agents may be administered in different amounts and at different times.

To achieve the desired therapeutic effect, compounds may be administered for multiple days at the therapeutically effective daily dose. Thus, therapeutically effective administration of agents/drugs to treat a condition or disease described herein in a subject requires periodic (e.g., daily) administration that continues for a period ranging from three days to two weeks or longer. Typically, agents/drugs will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds are not administered daily, so long as the administration is repeated frequently enough to maintain a therapeutically effective concentration of the agents/drugs in the subject. For example, one can administer the agents/drugs every other day, every third day, or, if higher dose ranges are employed and tolerated by the subject, once a week.

Optimum dosages, toxicity, and therapeutic efficacy of such compounds may vary depending on the relative potency of individual agents/drugs and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. HIV agents/drugs that exhibit large therapeutic indices are preferred. While agents/drugs that exhibit toxic side effects can be used, care should be taken to design a delivery system that targets such compounds to the HIV infected cells to minimize potential damage to normal cells and, thereby, reduce side effects. In addition, combinations of agents/drugs having synergistic effects described herein can be used to further reduce toxic side effects of one or more agents comprising a pharmaceutical composition of the invention.

The data obtained from, for example, cell culture assays and animal studies can be used to formulate a dosage range for use in humans The dosage of agents/drugs described herein lies preferably within a range of circulating concentrations that include the $ED_{50}$ with little or no toxicity. The dosage can vary within this range depending upon the dosage form employed and the route of administration. For any agents/drugs used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of compounds is from about 1 ng/kg to 100 mg/kg for a typical subject.

Following successful treatment, it may be desirable to have the subject undergo maintenance therapy to prevent the recurrence of the condition or disease treated. In some embodiments, a therapeutic maintenance regimen can be administered to treat the subject with HIV-1 based on the detected HIV-1 levels following additional quantification of latent HIV-1 levels from a sample obtained from the subject.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The invention is further illustrated by the following example, which is not intended to limit the scope of the claims.

Example 1

We developed a novel deep sequencing-based protocol (EDITS, Envelope Detection by Induced Transcription-based Sequencing) to measure RNA induction, capable of detecting inducible cell-associated HIV RNA. The EDITS Assay measures inducible HIV envelope RNA in infected cells, including patient-derived samples. The HIV envelope mRNA has been chosen because the splicing pattern covers a significant portion of the proviral genome, thus minimizing readouts from defective proviruses with large deletions (FIG. 1). Briefly, $1.25 \times 10^6$ resting memory cells from aviremic (<20 copies/ml) HIV-1-infected subjects are induced by one or more latency reversing agents (LRAs) and/or by engagement of the T-cell receptor (TCR). As shown in FIG. 2, the assay gives minimal background signals prior to induction by LRAs and is highly reproducible.

A great advantage of this method is that the PCR products obtained from cells treated by different LRAs, and from different patients, can be multiplexed (i.e., barcoded, pooled, and sequenced simultaneously). This saves time, sequencing costs, and allows accurate sample to sample comparisons since input cDNA levels are effectively normalized. Comparisons of readouts obtained by the much more laborious and expensive conventional qPCR and multiplexed sequencing (FIG. 2A) shows that they are both linear in equivalent ranges. Since high levels of HIV env mRNA expression also requires expression of Tat and Rev the background levels in this assay are minimal (FIGS. 2B, 2C, 3 and 4).

Figure 3:
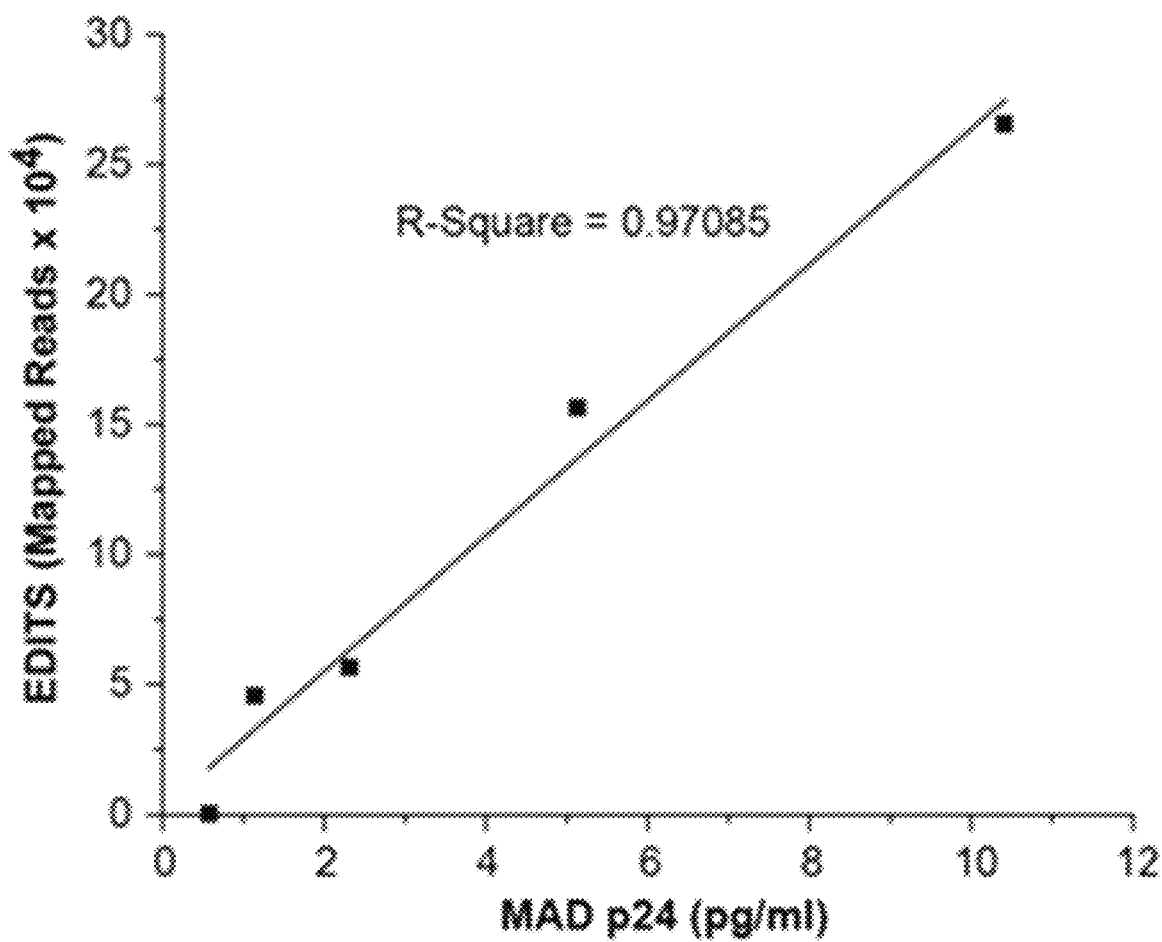
FIG. 3 Illustrates EDITS correlation with p24 release. Time course of spliced env RNA induction compared to the Merck MAD assay which measures p24 antigen released into the supernatant.

The readouts from the EDITS assay also correlate strictly with a unique digital immunoassay, Merck Antigen Detection Assay (MAD) that has been developed to quantify HIV p24 capsid protein with unprecedented sensitivity. The assay is 2,000-fold more sensitive than contemporary p24 assays with a lower limit of detection (LOD) of 3 fg/ml, and a lowest limit of reliable quantitation (LLRQ) of 14 fg/ml (FIG. 3). Despite the extreme sensitivity of the MAD assay it is approximately 10-fold less sensitive than the EDITS assay and is unable to detect signals with 24 hrs of proviral induction, when the EDITS assay is typically performed.

Figure 4:
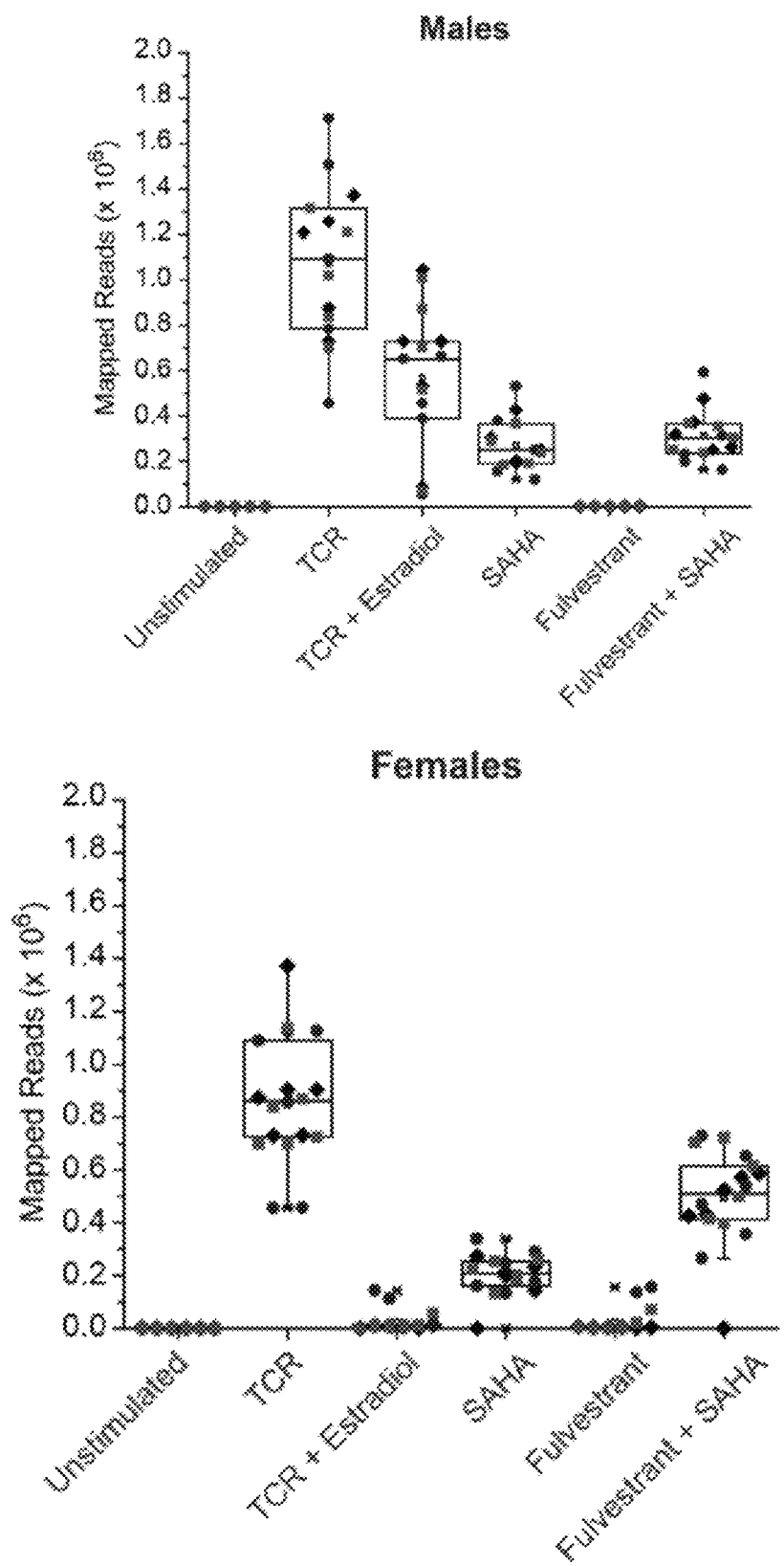
FIG. 4 illustrates Reproducibility of HIV RNA induction measurements by EDITS. Data represents determination from 5 male and 6 female donors who were well matched in terms of virological parameters including duration of suppression, CD4 nadir, degree of suppression, etc. The data is derived from three separate experiments (represented by the different colored symbols) 3 datasets run over a 4-month period using frozen samples. Samples were activated ex vivo by TCR induction in the presence and absence of Estradiol, which is a potent inhibitor of proviral reactivation, or SAHA, or the anti-estrogen Fulvestrant, or a combination of Fulvestrant and SAHA. Sample variance: Standard Deviation 18.6%, Standard Error 10.7%.

As shown in FIG. 4, the assay is highly reproducible with a standard deviation of 18.6%, and standard error 10.7% as seen in three separate experiments. Here, samples were from 11 leukapaks obtained from patients where clinical and virological data was collected, including pre-treatment viral load, CD4+ T-cell nadir, CD4+ T-cell count at the time of enrollment and residual HIV-1 viremia by single copy assay. We estimate that the assay can reproducibly detect reservoir size differences of 20%.

Figure 5A:
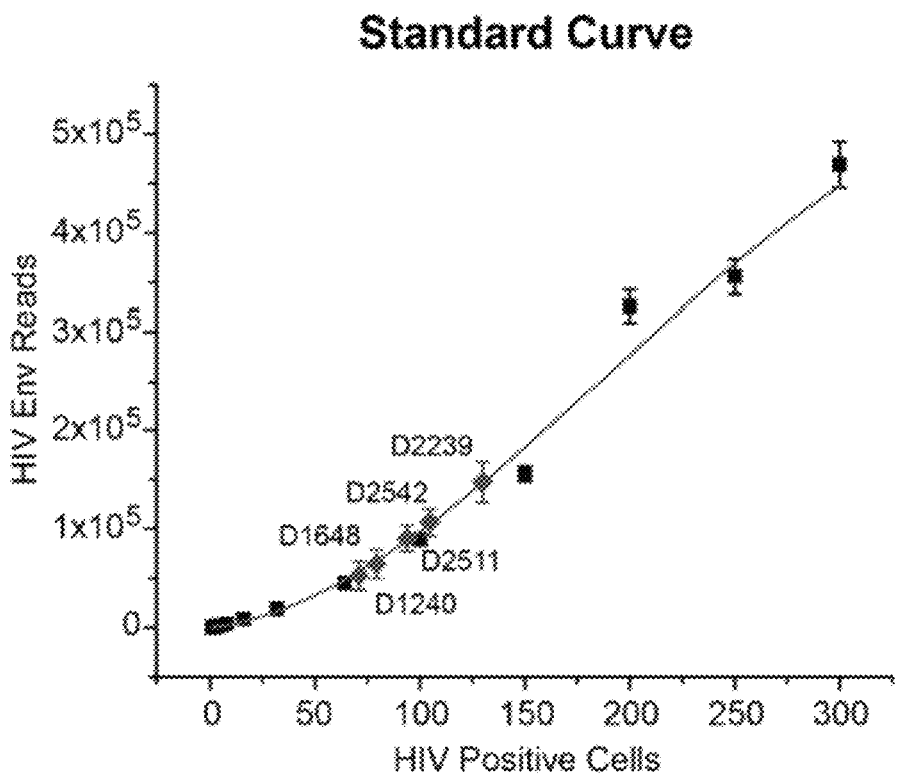
FIGS. 5(A-B) illustrate measurement of HIV reservoir by EDITS.
Figure 5B:
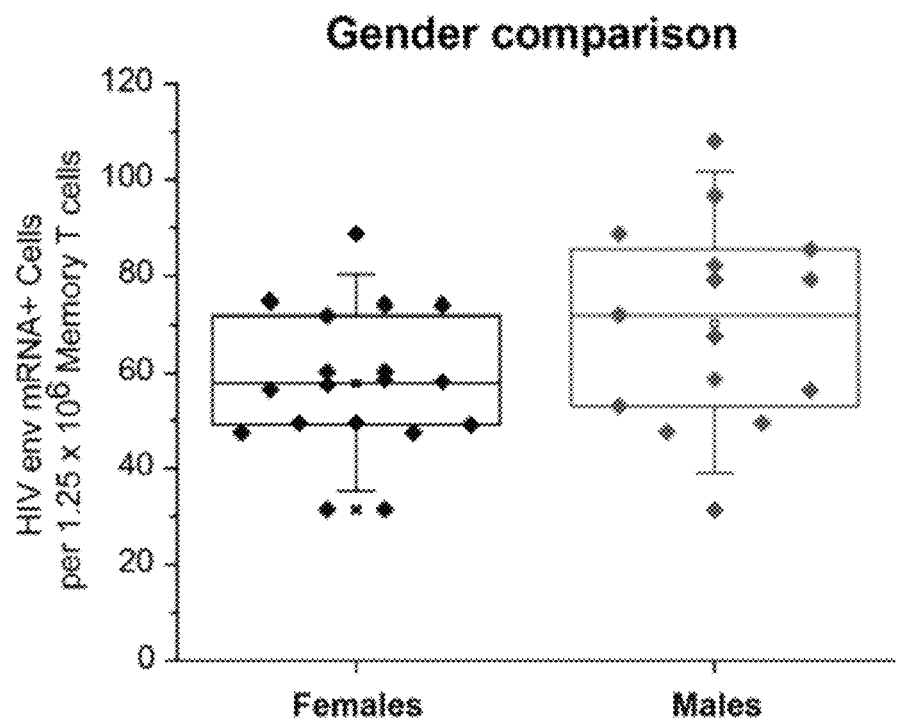

To convert mapped reads to estimate of the number of cells that are induced, we compared the reads to an internal calibration curve. The curve is generated by sorting known numbers of activated cells infected with recombinant viruses carrying a reporter gene (i.e., green-fluorescent protein, GFP). Typically, the curve extends from 1 to 300 cells per well. As shown in FIG. 5, the calibration curve is linear between 10 and 300 cells per sample using our standard amplification protocol. Additional sensitivity can be achieved using extended PCR amplifications. Thus the assay is able to provide a readout that is proportional to the number of activated cells in the peripheral circulation.

A potential limitation of the EDITS assay, which is shared by all PCR-based assays, is that it does not directly measure the induction of replication competent viruses. However, replication-competent viruses represent a subset (10% to 50%) of the inducible RNA pool and levels of unspliced cellular HIV-1 RNA after induction correlate with virion production (p=0.67, P<0.001), and there is no way of knowing the efficiency of the various proviral induction in these protocols. Consequently, infectious RNA assays may seriously underestimate the inducible pool. On the other hand, the RNA induction assays may overestimate the pool by including sequences derived from deleted proviruses. We estimate that efficiency of activation of RNA from proviruses using strong LRAs such as TCR activation or mitogen activation (e.g., Concanavalin A) can be greater than 75%. We have been able to minimize, but not eliminate, this possibility by choosing widely space primers for the spliced mRNA assays. In the case of the EDITS assay we estimate the signal from defective proviruses is between 25% and 50%. Despite the limitations described above, we believe that the EDITS assay represent the best approach to compare various induction regimens in clinical samples because of their high reproducibility, excellent signal to noise and conservative sample requirements. Table 1 summarizes the main parameters of the EDITS assay. It is capable of detecting as few as 5 induced cells per $10^6$ cells, highly reproducible, utilizes minimal materials and has realistic costs.

TABLE 1

Validation Parameters EDITS Assay

| | |
|---|---|
| Linear range (units) | 50 to 100 cells per $10^6$ cells |
| Sensitivity (limit of detection) | 5 to 10 cells per $10^6$ cells |
| Precision (variability within replicates) | +/−10% |
| Specificity (ability to detect only the intended target) | 100% |
| Accuracy (ability to detect positive control samples) | >95% |
| Biological Variation (variation in longitudinal samples) | Not tested |
| Sample variance: | Standard Deviation 18.6%, Standard Error 10.7%. |
| Minimal sample requirements (singlicate assay) | $10^6$ memory cells |
| Ability to use fresh or frozen samples | Yes |
| Detection in blood/fluids/tissue compartments | Detection in blood and tissue compartments |
| Subtype Coverage | B subtype only (other primer sets are being developed for A, D, C) |
| Clinical sensitivity (% positivity among known HIV+ people) | Unknown |
| Turn-around time to perform assay | 7 days |
| Cost | <$200 per sample |

Edits Assay in Detail

Figure 6:
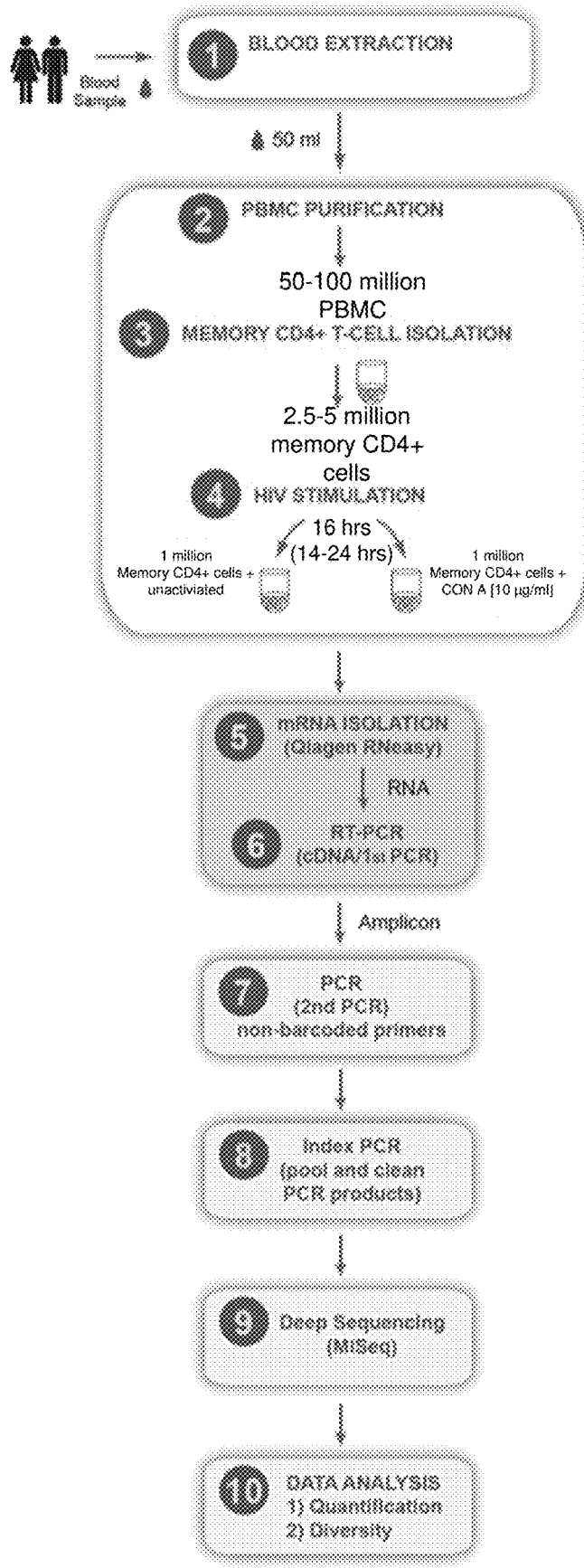
FIG. 6 illustrates an overall protocol for the EDITS assay.

FIG. 6 summarizes the protocol of the EDITS assay. Briefly, blood is collected from an HIV-infected individual and peripheral blood mononuclear cells (PBMCs) are purified. $CD4^+$ memory cells are negatively isolated using robotic magnetic bead isolation technology (Stemcell, 19157RF) and allowed to equilibrate in RPMI with 10% FBS, Primocin and 30 IU/ml of IL-2 overnight. 1.25 million cells are stimulated with one or more LRA (e.g., Concanavalin A) for 24 hours.

Total RNA is isolated using Qiagen RNeasy purification system (Qiagen, 74134) following manufactures protocol, eluting into 20 μl of RNAse free water. The entire sample is then used as template in a one-step RT-PCR reaction (Thermoscientific, AB-4104A) using the following cycling conditions: 1 cycle at 50 C for 15 min, 1 cycle at 95 C for 15 min, 35 cycles of 95 C for 15 sec, 60 C for 30 sec and 72 C for 30 sec. Primers were designed to bind to either side of the HIV Env RNA splice junction at position 546-565 for Singly Spliced Forward primer F (5'-gcttcaagtagtgtgtgccc-3') (SEQ ID NO:1) and position c7609-c7630 Singly Spliced Reverse primer (5'-ctgaagatctcggactcattgt-3') (SEQ ID NO:2). Using these primers allows only the detection of late viral transcripts, eliminating any potential proviral DNA amplification. The primer binding regions are located in highly conserved regions of HIV based on the Los Alamos National Laboratory HIV Database.

After cDNA synthesis and PCR, 2 ul of the reaction is used as template for a subsequent round of nested PCR using a high fidelity Phusion Flash polymerase (Thermoscientific, F548). The amplification protocol is as follows: 1 cycle at 95 C for 30 sec, 35 cycles of 95 C for 1 sec, 62 C for 5 sec and 72 C for 5 sec and 1 cycle of 72 C for 1 minute. The nested primers were designed to bind to positions 6025-6046 (5'-caagcttctctatcaaagcag-3') (SEQ ID NO:3) and 6373-6394 (5'-tctgatgcacaaaatagagtgg-3') (SEQ ID NO:4). Each forward and reverse nested primers also contain one barcode and two adapter sequences to allow for multiplexing of samples and bi-directional deep sequencing, respectively.

PCR products are then pooled and cleaned up using GeneJET NGS cleanup kit (Fisher Scientific, FERK0852) to remove primers and non-amplified products. 300 pg of the pooled library is then deep sequenced using any of the instruments currently available, i.e., Ion Torrent, Illumina, Pacific Biosciences, or Oxford Nanopore systems following the manufacturer protocol.

Fastq files are analyzed using a proprietary pipeline (bioinformatics tool) to not only quantify the amount of HIV-1 present in any given sample but also to determine viral diversity.

Example 2

Sex-Based Differences in HIV-1 Reservoir Activity and Residual Immune Activation Biological sex modulates immune-mediated protection from pathogens and autoimmunity leading to differences in the acquisition and pathogenesis of multiple infections, the efficacy of vaccines and a female predominance in some autoimmune diseases. Sex differences have been specifically observed in HIV-1 viral dynamics and immune responses. These immunologic sexual dimorphisms are driven by multiple factors, including genetic differences derived from the chromosomal complement, sex-specific epigenetic profiles, and the influence of sex hormones.

Higher plasma HIV-1 RNA levels in men versus women are evident proximal to seroconversion. Importantly, despite this lower level of HIV-1 RNA in women, disease progression rates were comparable in both sexes in the pre-treatment era. Viral load differences attenuates as disease progresses, but there is evidence for sex-driven effects on plasma HIV-1 RNA. The mechanisms governing the interaction between HIV-1 RNA levels and disease progression may include differences in T-cell subset distribution and available targets, along with hormonal modulation/sex-specific differences in immune responses and direct inhibition of viral transcription by estrogen.

Immune activation is also discordant by sex. Women have higher T-cell activation for a given level of plasma viremia, higher levels of IFNα production by plasmacytoid dendritic cells (pDCs) after TLR7 stimulation and higher expression of interferon-stimulated genes for a given level of HIV-1 RNA. Taken together, the data demonstrate that the immune response to HIV-1 is sex specific.

There is a relatively little data to define sex differences in the HIV-1 virus reservoir size and activity, or in cellular immunophenotypes after the initiation of antiretroviral therapy (ART), which is highly efficacious in both men and women. Two cross-sectional studies of ART-treated individuals have reported that women were more likely to have lower levels of HIV-1 DNA than men, and several studies have reported sex differences in soluble inflammatory markers linked to non-AIDS morbidity and mortality. However, no study has prospectively and systematically assessed sex differences in the immune phenotype and HIV-1 reservoir and women are significantly underrepresented in clinical trials relevant to HIV-1 cure.

To address this knowledge gap, we prospectively enrolled a cohort of well-matched, HIV-1-infected men and women with ART-suppressed viremia and to measure the frequency, activity, and inducibility of latently infected cells along with cellular markers of immune activation. We identify significant differences between men and women that should inform the design and interpretation of clinical trials testing HIV-1 curative interventions.

Methods

Study Design and Participants

Study participants were enrolled through the UCSF SCOPE OPTIONS cohort and the San Francisco General Hospital Positive Health Practice ("Ward 86") HIV Clinic between March 2014 and April 2015. All provided informed consent and the study was reviewed and approved by the UCSF institutional review board. Women and men on fully suppressive ART were prospectively enrolled matched by duration of viral suppression, absolute CD4$^+$ T-cell count and nadir, and early initiation of ART (<six months after infection with continuous suppression). Unusual clinical phenotypes (e.g., early start of therapy or viremic control defined as a majority of plasma viral loads <10,000 copies, CMV serostatus) were considered and balanced when possible. No elite controllers (untreated viral load<400 copies) were included. Systemic hormonal therapy was an exclusion criterion. Coinfection data, demographics, ART, menstrual status and reproductive history were collected. PBMCs and plasma were stored for analysis; a subset of participants (n=6 of each sex) returned for leukapheresis. All participants provided informed consent and the study was reviewed and approved by the UCSF Institutional Review Board.

Virologic Measures

CD4$^+$ T-cells were isolated from cryopreserved PBMCs and the frequencies of cells harboring total and integrated HIV-1 DNA (tHIV and iHIV) were measured relative to CD3 copy number. Cell associated (CA) unspliced (usHIV) RNA was quantified and multiply-spliced (msRNA) was measured using the identical semi-nested PCR with different primers. Low level viremia was quantified from seven milliliters of plasma with PCR amplification targeting a conserved, untranslated HIV-1 gag RNA sequence (the HMMCgag assay). Inducible HIV-1 RNA was measured using the TILDA assay; briefly, purified CD4$^+$ T-cells are stimulated maximally with PMA/ionomycin, serially diluted, lysed and HIV-1 msRNA measured with a two-step RT-PCR. Maximum likelihood estimates based on the number of positive wells are used to determine the frequency of cells harboring inducible HIV-1. A modified version of the EDITS assay was used to quantify spreading viral infections. Purified CD4$^+$ T-cells were stimulated with the mitogen Concanavalin A (Con A) in the absence or presence of 1 µM Raltegravir (to block spreading infection) and absence or presence of 300 pg/ml 17β-estradiol. Newly infected cells were determined after nine days as the increase in HIV RNA+ cells in the absence of Raltegravir.

Immunologic Measures

Cryopreserved PBMCs were batch processed and stained with panels for T-cell activation and exhaustion, monocyte, NK and dendritic cell phenotyping. Gating strategies and antibody panels available in.

Hormone Levels

Plasma samples were analyzed in batch by liquid chromatography-mass spectrometry for levels of circulating progesterone and 17β-estradiol (Brigham and Women's Hospital Research Assay Core).

Statistical Analysis

Virologic outcomes were assessed using negative binomial regression to generate estimates of the effect of female sex on the outcome variable, including a measure of input as the exposure variable (e.g., 18s RNA for HIV-1 RNA measures, plasma volume for HMMC gag measures). This method accounts for the lower precision of measures at the lower limits of detection and in the setting of low input amounts. Multivariate models were built by stepwise addition of predictor variables, with sex forced as a covariate, until no remaining unselected candidate predictor had $p<0.05$ when added to the current model. Pre-treatment maximum viral load was excluded from models of residual viremia, as it may be on the causal pathway of sex's influence on residual viremia. Mixed effects negative binomial regression was used to assess the fold effect of sex on the ratios of HMMC gag and HIV-1 RNA measures to the iHIV DNA measure, also as previously described. TILDA values were compared by maximum likelihood estimation on the data from all individual experimental wells. For plotting purposes only, one person with no positive wells was given a TILDA value of 2. To estimate the effect of female sex on the TILDA/iHIV ratio, we performed customized maximum likelihood modeling of the well-by-well TILDA results together with the detailed iHIV data. For TILDA, we used the standard single-hit likelihood calculations for limiting dilution assays, and for iHIV we used a negative binomial model with constant dispersion and with the input to the assay (CD3) as the exposure. The model included normally distributed random effects that modeled between-person variation in log(TILDA) and log(TILDA: iHIV ratio). EDITS data was obtained from a single sequencing chip and differences between data sets were evaluated by Mann-Whitney statistics.

Virologic and immunologic parameters were assessed for associations using Spearman rank correlations in the overall cohort and within each sex. P-values for differences in correlations between men and women were obtained by standard calculations using the Fisher z-transformation Immune subsets were compared between sexes by Mann Whitney testing, and analyses were repeated excluding the CMV-seronegative subjects (n=5 women).

Nominal p-values are reported without adjustment for multiple testing; adjustment requires that results expected to biologically co-vary (e.g., inverse variations in T-cell subsets) detract from each other, when they should be reinforcing. We present the full dataset, including exploratory findings, indicating where the unadjusted $p<0.05$.

Results

Cohort Characteristics

Demographic and clinical features of the participants (n=26 women and n=26 men) are shown in Table 2. Maximum pretreatment viral load (VL) was not matched, and the median value in women was 0.13 log lower than men (Mann Whitney $p=0.14$). There were comparable levels of active hepatitis C infection and injection drug use, and comparable rates of viremic controllers (defined as majority of pre-ART viral loads <10,000, (23% men, 35% women, Fisher's exact p=0.54)). The CMV seropositive rate was higher in male participants than in the female group (100% men, 81% women, Fisher's exact test p=0.05). Among women participants, 73% of the cohort reported regular menstrual cycles and all had detectable 17β-estradiol and progesterone levels. Of patients with amenorrhea, 2 had history of ovary-sparing hysterectomy and 2 had a history of IUD placement (>6 months prior to study enrollment). Three additional women reported irregular menses; in 2 of these women the hormone levels and clinical assessment suggested an anovulatory cycle at the time of sampling.

Table 2 shows demographic and clinical characteristics of the cohort. Observations were available for all subjects (n=26 women and 26 men) with the exception of maximum pretreatment viral load; this value was missing 5 observations, all from the female subjects. Definitions for timing of ART initiation: Early, continuous is therapy initiated months from estimated date of infection with continuous suppression; Late is therapy initiated >6 months after estimated date of infection; Early, interrupted or unknown includes participants with unknown timing of therapy initiation and those who started within 6 months of infection but had interruptions with viral rebound after that point.

differences in HIV DNA content of CD4+ T-cells between men and women (FIG. 8A, Table 3); women had an estimated a 1.39 fold higher level of iHIV DNA, but with a wide confidence interval (p=0.47, CI 0.57-3.37), with similar estimates for tHIV DNA (1.38 fold increase in women, p=0.39, CI 0.67-2.84). Models incorporating additional clinical characteristics also estimated similarly modest sex differences, not reaching statistical significance.

Table 3 shows the effect of female sex on virologic measures. Negative binomial regression in univariate and multivariate models to assess the quantitative influence of female sex on virologic measures.

TABLE 3

| HIV-1 reservoir measure | Female fold effect | Confidence Interval | p value |
|---|---|---|---|
| iHIV DNA | 1.39 | 0.57-3.37 | 0.47 |
| tHIV DNA | 1.38 | 0.67-2.74 | 0.39 |
| SCA (HMMCgag) | 1.02 | 0.38-2.72 | 0.974 |
| SCA (HMMCgag) adjusted for: duration of suppression treatment interruptions | 0.23 | 0.08-0.72 | 0.011 |

TABLE 2

| Cohort Characteristics | Men | Women |
|---|---|---|
| Age in years, median (IQR) | 43 (33-48) | 41 (35-48) |
| CD4 nadir cells/uL, median (IQR) | 270 (131-442) | 214 (111-317) |
| CD4 at sampling cells/uL, median (IQR) | 646 (544-825) | 677 (530-861) |
| Duration of infection years, median (IQR) | 7 (4.0-11.5) | 8 (4.8-14.3) |
| Duration of viral suppression years, median (IQR) | 3.3 (2.1-6.7) | 2.8 (1.8-4.3) |
| Max pretreatment viral load, median (IQR) | 4.74 (4.4-5.4) | 4.61 (3.8-5.2) |
| Controller (majority of pretreatment VL < 10,000) | 6 (23) | 9 (35) |
| CMV positive, n (%) | 26 (100) | 21 (81) |
| Active HCV infection, n (%) | 2 (7.7) | 1 (3.8) |
| IDU, n (%) | 3 (12) | 5 (19) |
| Timing of ART initiation | | |
| Early, continuous | 1 (4) | 1 (4) |
| Late | 20 (77) | 20 (77) |
| Early and interrupted or unknown | 5 (19) | 5 (19) |
| ART regimen, n (%) | | |
| PI | 3 (12) | 9 (35) |
| NNRTI | 12 (46) | 11 (42) |
| INSTI | 9 (35) | 6 (23) |
| PI/INSTI | 1 (4) | 0 |
| NNRTI/INSTI | 1 (4) | 0 |
| Race, n (%) | | |
| White | 9 (35) | 8 (31) |
| Black | 7 (27) | 6 (23) |
| Hispanic | 4 (15) | 4 (15) |
| Asian | 2 (8) | 3 (12) |
| Native American | 1 (4) | 0 |
| Mixed/Multiracial/Other | 3 (11) | 5 (19) |

Abbreviations:
IDU = injection drug use,
PI = protease inhibitor,
NNRTI = non-nucleoside reverse transcriptase inhibitor,
INSTI = integrase strand transfer inhibitor.

Frequencies of CD4+ T-Cells Harboring HIV-1 DNA were Comparable Between Sexes

Isolated CD4+ T-cells were analyzed for integrated and total HIV-1 DNA. iHIV and tHIV were highly correlated with each other in the overall cohort and within each sex. iHIV DNA correlated with peak pretreatment viremia overall (r=0.48, p=0.001) and within each sex (women r=0.63, p=0.002; men r=0.46, p=0.018), and with nadir CD4+ T-cell count and proximal pretreatment viral load, with similar relationships for tHIV DNA. There were no significant TABLE 3-continued

| HIV-1 reservoir measure | Female fold effect | Confidence Interval | p value |
|---|---|---|---|
| SCA (HMMCgag):iHIV DNA | 0.43 | 0.20-0.91 | 0.027 |
| CA msHIV RNA | 0.16 | 0.05-0.51 | 0.002 |
| CA msHIV RNA adjusted for: CD4nadir controller phenotype | 0.25 | 0.09-0.71 | 0.009 |

TABLE 3-continued

| HIV-1 reservoir measure | Female fold effect | Confidence Interval | p value |
|---|---|---|---|
| CA msHIV RNA:iHIV DNA | 0.29 | 0.13-0.64 | 0.002 |
| CA usHIV RNA | 0.65 | 0.29-1.43 | 0.280 |
| CA usHIV RNA adjusted for: max pretreatment viral load CD4 nadir race early treatment initiation controller phenotype | 0.68 | 0.35-1.32 | 0.253 |
| CA usHIV RNA:iHIV DNA | 0.52 | 0.25-1.07 | 0.08 |

HIV-1 Reservoir Activity Lower in Women Compared to Men

Figure 8A:
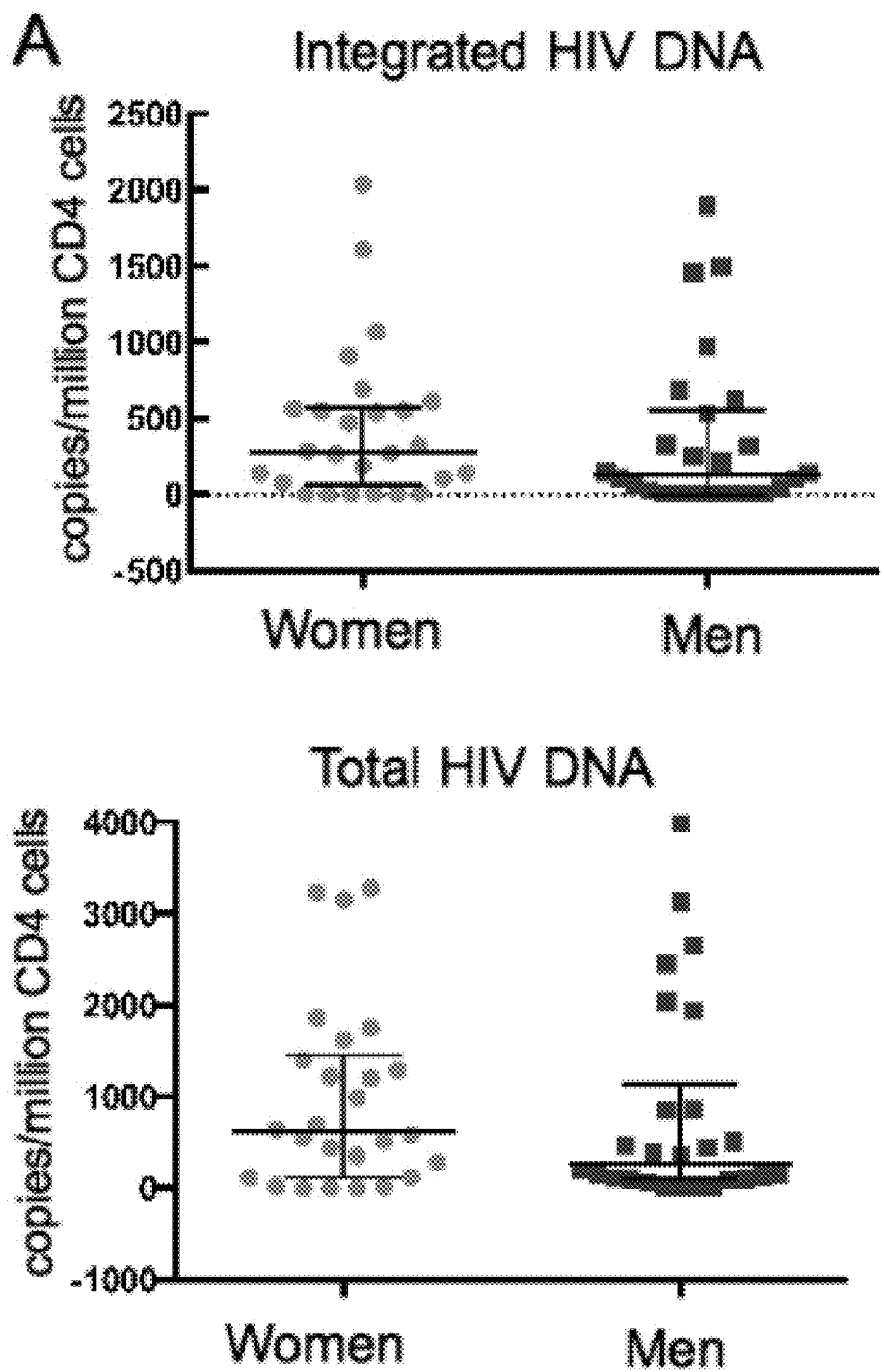
FIGS. 8A-D illustrate a comparison of virologic markers by sex. (A) Integrated and total DNA measured in isolated CD4 cells were comparable between men and women. (B) Low level viremia measured by single copy assay was lower in women than in men. (C) msHIV RNA was lower in women. (D) There was no statistically significant difference in the level of usHIV RNA. For all values, median and interquartile ranges are shown.
Figure 8B:
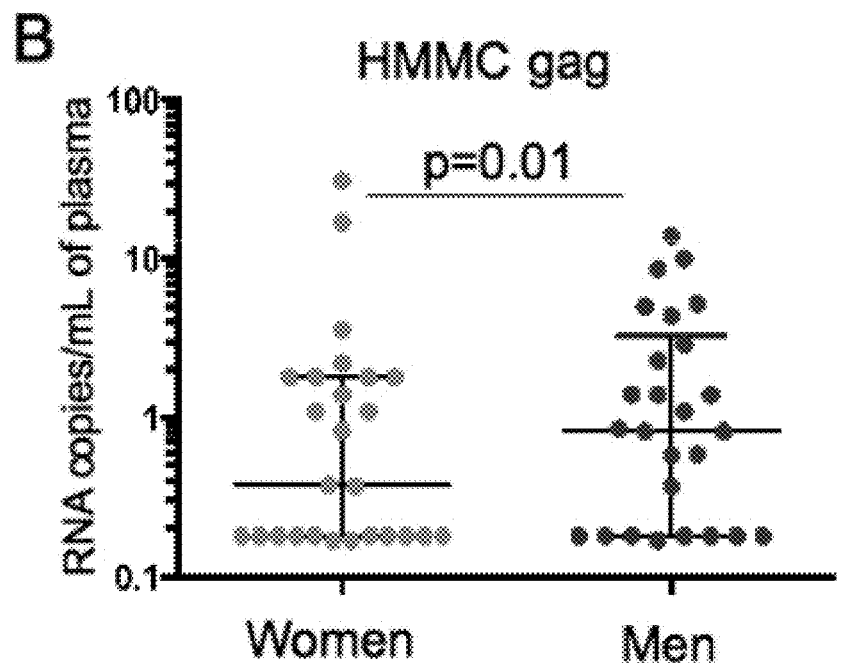

All participants were suppressed to <75 copies of HIV-1 RNA per mL plasma by clinical assays. Women had a 77% lower level of residual plasma viremia by HMMCgag in a multivariate model controlling for years of viral suppression and number of treatment interruptions (fold-effect=0.23, CI 0.08-0.72, p=0.011) (FIG. 8B, Table 4). The ratio of plasma viremia to iHIV DNA averaged 57% lower in women compared to men in a univariate model (fold-effect=0.43, CI 0.20-0.91, p=0.027).

Table 4 shows the correlations between $CD4^+$ T cell parameters and virologic measures. Spearman's rho values are shown for parameters that reached the level of p<0.05 when assessed for all participants in the cohort.

TABLE 4

| | Virologic measure | | | |
|---|---|---|---|---|
| T cell parameters | iHIV DNA | HMMCgag | usHIV RNA | msHIV RNA |
| CD4+ T cells | −0.45 | | −0.40 | |
| CD4+27+28+45RA− HLA-DR+/CD38− | 0.46 | 0.29 | 0.40 | 0.38 |
| CD4+HLA-DR+/CD38− | 0.41 | | 0.35 | |
| CD4+27+28+45RA+HLA-DR+/CD38− | 0.35 | | 0.36 | |
| CD4+27+28+45RA−HLA-DR−/CD38+ | −0.34 | | | |
| CD4+27−28+45RA−HLA-DR+/CD38− | 0.34 | 0.30 | | |
| CD4+27+28−45RA−HLA-DR−/CD38+ | −0.29 | | | |
| CD4+27+28−45RA−HLA-DR+/CD38− | 0.29 | | 0.35 | |
| CD4+27−28+45RA−HLA-DR−/CD38− | | −0.38 | | |
| CD4+27−28+45RA− HLA-DR+/CD38+ | | 0.32 | | |
| CD4+27+28−45RA+CCR5+ | | | 0.43 | |
| CD4+27+28−45RA−CCR5+ | | | 0.36 | |
| CD4+CCR5+ | | | 0.29 | |
| CD4+27−28−45RA+PD1+ | | | | −0.36 |
| CD4+27+28−45RA+ HLA-DR−/CD38− | | | | −0.31 |
| CD4+27+28−45RA+PD1+ | | | | −0.29 |

Figure 8C:
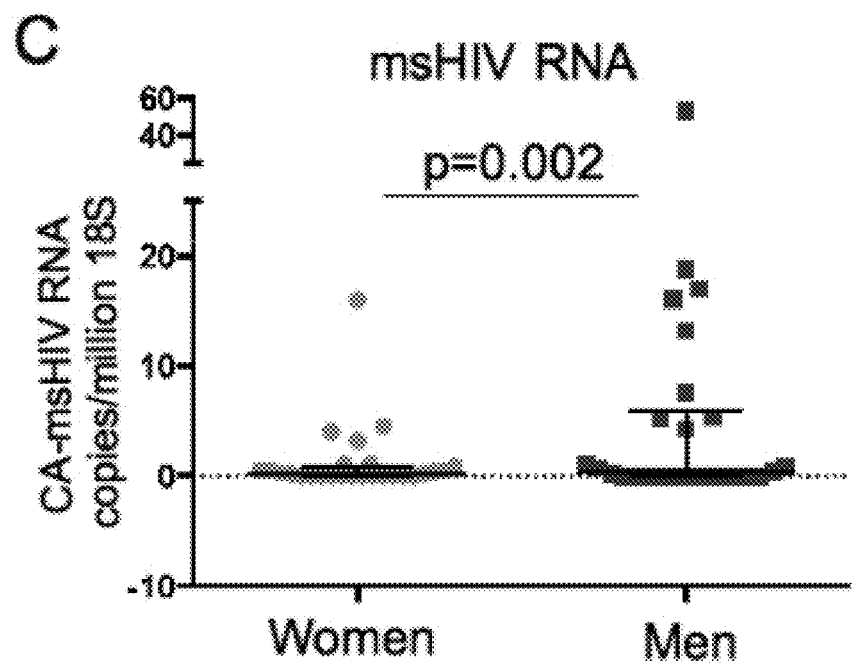
Figure 8D:
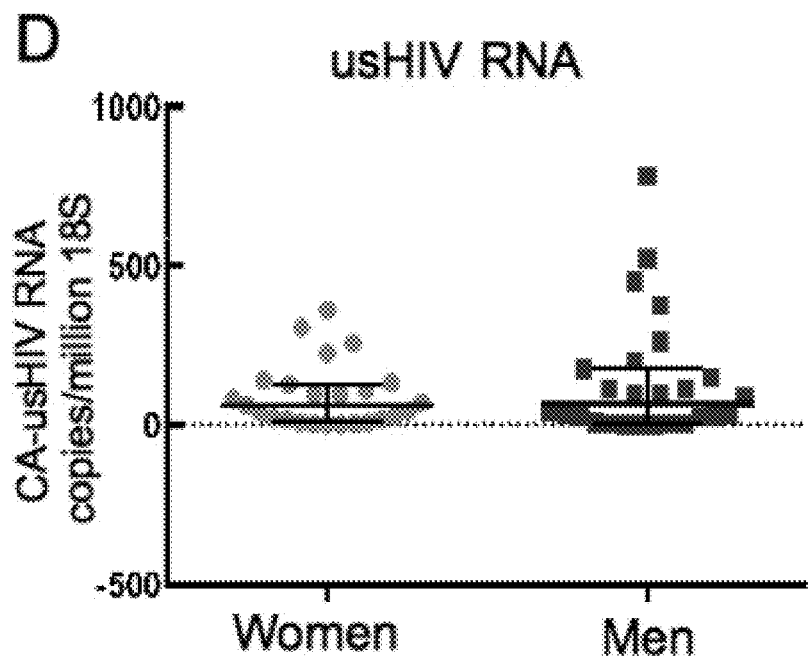

We measured CA usHIV and msHIV RNA from $CD4^+$ T-cells. Negative binomial regression found a 6-fold lower level of msHIV RNA in women (fold-effect=0.16, CI 0.05-0.51, p=0.002) (FIG. 8C, Table 3). In a multivariate model adjusting for nadir CD4 and controller phenotype (both associated with msHIV RNA at p<0.05), there was a 4-fold lower level of msHIV RNA in women (fold-effect=0.25, CI 0.09-0.71, p=0.009). The ratio of msHIV RNA to iHIV DNA was 3.4 fold lower in women (fold effect 0.29, CI 0.13-0.64, p=0.002). Univariate negative binomial regression estimated 35% lower level of usHIV RNA in women, but with a wide confidence interval (fold-effect=0.65, CI 0.29-1.43, p=0.28) (FIG. 8D, Table 3). A multivariate model (early start of ART, log maximum pretreatment plasma HIV-1 RNA, CD4 nadir, controller phenotype, race) estimated a similar fold change, again without achieving statistical significance (fold-effect=0.68, CI 0.35-1.32, p=0.25). Sex comparison of the ratio of usHIV RNA to iHIV DNA level was similar (fold-effect=0.52, CI 0.25-1.07, p=0.08). Taken together, despite similar measures of HIV DNA, women had less measurable virus activity than men by both the single copy assay for plasma viremia and the level of msRNA in $CD4^+$ T-cells.

Subset Analysis of Ex Vivo Reservoir Induction

Figure 9A:
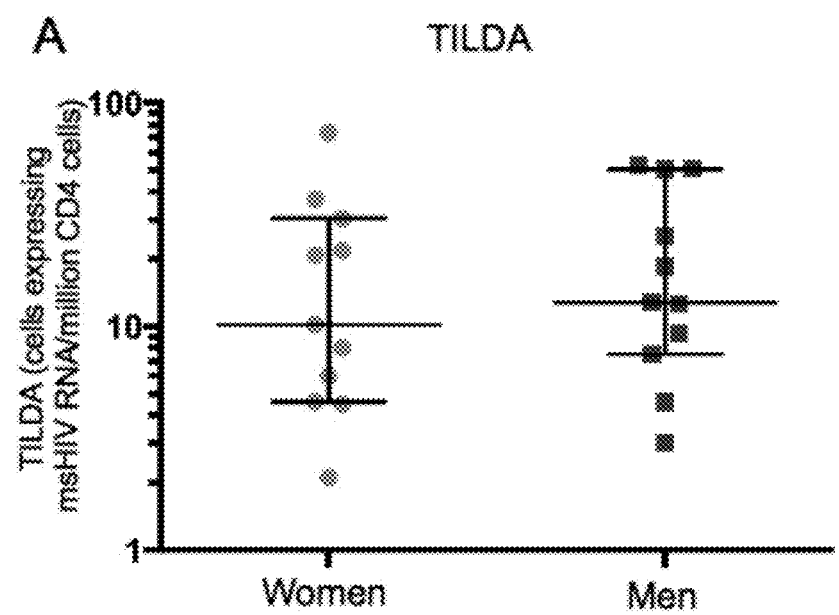
FIGS. 9A-B illustrate sex comparison of the inducible reservoir as measured by the TILDA assay in isolated resting CD4+ T-cells. (A) Comparison of TILDA values between men and women did not show a statistically significant difference. (B) When normalized to iHIV DNA levels, female subjects had generally lower ratios of TILDA:iHIV DNA, although this did not achieve statistical significance.
Figure 9B:
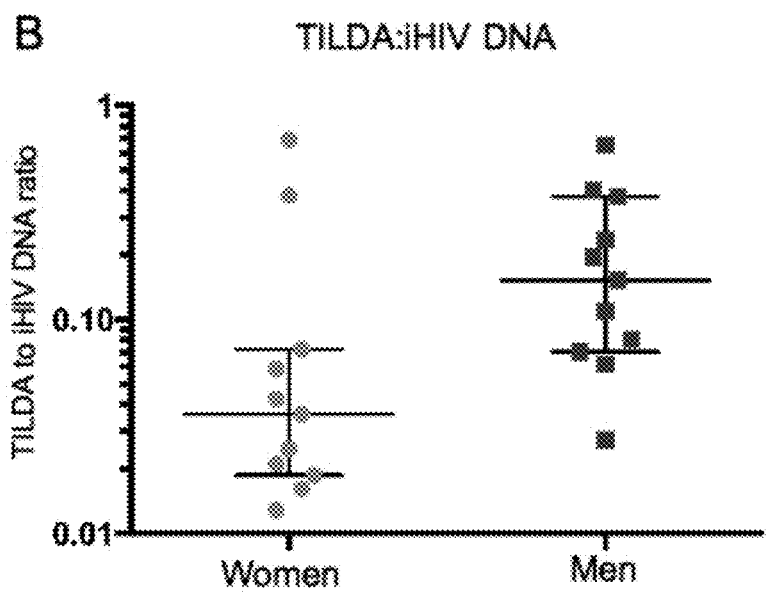

In a subset of subjects (n=11 men and 11 women), ex vivo induction of spliced tat/rev transcripts after T-cell activation was measured with the TILDA assay. TILDA values did not differ between men and women in this subgroup; maximum likelihood estimate on raw data gave female status a fold effect of 0.81 (CI of 0.33-2.0, p=0.63) (FIG. 9A). We then compared the ratio of TILDA:iDNA values, using customized maximum likelihood modeling of the well-by-well TILDA results. In this subset, women were estimated to have approximately 2-fold lower ratio of inducible HIV-1 RNA relative to the iHIV DNA levels, but again with wide confidence intervals (female sex fold effect 0.45, CI 0.16-1.21, p=0.11, FIG. 9B).

As a complementary method to evaluate sex differences $CD4^+$ T-cells from a subset of men (n=6) and women (n=6) who underwent leukapheresis were evaluated for the level of inducible replication competent virus using a modified EDITS assay (FIG. 10). Purified $CD4^+$ memory cells were stimulated for 9 days to induce HIV transcription in the presence or absence of raltegravir and number of HIV $RNA^+$ cells was quantified by EDITS. In the presence of raltegravir, viral spread was blocked and there were 74 RNA positive cells per million for the women and 80 for the men; values comparable to those obtained from an overnight induction by TCR activation, but not statistically different between the sexes. In the absence of raltegravir, there were 348 RNA positive cells per million for the women and 457 RNA positive cells per million for the men, indicating spreading infection. Addition of 300 pg/ml 17β-estradiol potently blocked both HIV RNA induction (p=0.00039) and spreading infection (p=0.00052) in women compared to men, consistent with our earlier observation that the estrogen receptor-1 (ESR-1) can act as a repressor of HIV transcription.

Lower Levels of Cellular Immune Activation and PD-1 Expression in Women Compared to Men A pre-specified primary analysis of immunophenotypes compared T-cell activation, antigen experience/exhaustion, and expression of CCR5 on bulk and memory T-cells. Measures of activation by both HLA-DR/CD38 coexpression and antigen experience/exhaustion as indicated by PD-1 expression were higher in men in both total and memory CD4$^+$ and CD8$^+$ T-cells (FIG. 11). CCR5 expression percentage was higher only on bulk CD8$^+$ T-cells. T-cell comparisons were also assessed excluding CMV seronegative individuals (n=5, all women); the majority remained statistically significant. In contrast, the distribution of the innate immune cell populations of NK cells, monocytes, myeloid dendritic cells (mDCs) and plasmacytoid dendritic cells (pDCs) was not statistically different by sex.

Sex Specificity of Relationships Between T-Cell and Viral Parameters

All subsets of T-cells, measures of activation, differentiation and exhaustion were assessed for associations with virologic measures by Spearman rank correlation. Multiple correlations between CD4$^+$ (Table 4) and CD8$^+$ T-cells (Table 5) and virologic parameters were observed in the overall cohort. This finding is in marked contrast to the lack of identified associations at a p<0.05 level between any of the innate immune subsets/activation markers and virologic measures.

Table 5 shows the correlations between CD8$^+$ T cell parameters and virologic measures. Spearman's rho values are shown for parameters that reached the level of p<0.05 when assessed for all participants in the cohort.

overall cohort. The activated transitional memory CD8$^+$ CD27$^+$28$^-$45RA$^-$HLA-DR$^+$CD38$^+$ population was positively correlated with the SCA values in all analyses (Spearman's rho overall cohort r=0.47, p=0.0005, men only r=0.46, p=0.02, women only r=0.46, p=0.02, women with CMV-seronegatives excluded r=0.45, p=0.04) (FIG. 4B).

Within women, we analyzed the relationship of circulating levels of 17β-estradiol and progesterone to immune and virologic parameters. This analysis identified only an association between these hormones and the circulating percentage of myeloid dendritic cells (mDCs) (17β-estradiol r=0.42, p=0.036; progesterone r=0.55, p=0.005). Overall, associations between T-cell parameters and virologic measures displayed sex specificity.

In one of the first studies to systematically examine sex differences in immune responses among HIV-infected individuals on ART, using a matched cohort of prospectively-enrolled men and women, we identify key differences by sex in residual virus activity and cellular immune activation phenotypes. These observations suggest that curative interventions may reveal important differences in virologic and immunologic outcomes by sex, requiring careful attention to enrolling adequate number of women in cure studies to report sex-delineated outcomes.

In contrast to prior studies, the overall HIV-1 DNA levels in men and women in this cohort were comparable. The prior studies measured HIV-1 DNA levels in PBMCs, while we

TABLE 5

| T cell parameters | Virologic measure | | | |
|---|---|---|---|---|
| | iHIV DNA | HMMCgag | usHIVRNA | msHIVRNA |
| CD8+ T cells | 0.49 | | 0.44 | |
| CD8+CCR5+ | 0.28 | | 0.31 | |
| CD8+27+28−45RAHLA-DR+/CD38− | 0.31 | | | |
| CD8+27−28−45RA+HLA-DR+/CD38− | 0.32 | | | |
| CD8+27−28+45RA+HLA-DR+/CD38− | 0.33 | | | |
| CD8+ HLA-DR+/CD38− | 0.34 | | | |
| CD8+27+28+45RA−HLA-DR+/CD38− | 0.35 | | | |
| CD8+27+28−45RA+HLA-DR+/CD38− | 0.38 | | | |
| CD8+27−28+45RA− HLA-DR+/CD38− | 0.45 | | | |
| CD8+27−28+45RA− | | | | 0.40 |
| CD8+27−28+45RA−HLA-DR−/CD38− | | −0.29 | | |
| CD8+27+28−45RA+HLA-DR+/CD38+ | | 0.28 | | |
| CD8+27+28−45RA− HLA-DR+/CD38+ | | 0.47 | | |
| CD8+27+28−45RA− HLA-DR−/CD38− | | −0.43 | | |
| CD8+27+28+45RA− HLA-DR−/CD38− | | −0.34 | | |
| CD8+27−28−45RA−HLA-DR−/CD38− | | −0.31 | | |
| CD8+27+28−45RA−CCR5+ | | | 0.41 | |
| CD8+27+28−45RA+CCR5+ | | | 0.37 | |
| CD8+27−28−45RA+CCR5+ | | | 0.35 | |
| CD8+27−28−45RA−CCR5+ | | | 0.30 | |
| CD8+27−28+45RA+HLA-DR−/CD38+ | | | −0.28 | |

Exploratory analysis revealed distinct relationships between the T-cell parameters and virologic measures when men and women were considered separately. Again, there were no statistically significant relationships between innate cell phenotypes and virologic measures. For iHIV DNA, only bulk CD4$^+$ and CD8$^+$ T-cell percentage correlated in women whereas correlations were seen between iHIV and multiple T-cell subsets in men (FIG. 11A); correlation differences were statistically different at p<0.05 for several subsets. Excluding the CMV-seronegative women yielded largely consistent results, with a few unique associations.

Of note, the CD4$^+$CD27$^+$CD28$^+$CD45RA$^-$HLA-DR$^+$CD38$^-$ subset correlated with all virologic measures in the measured HIV-1 DNA in CD4$^+$ T-cells; sex variation in lymphocyte percentages may help to explain the discrepant findings. Alternatively, our prospective design and matching on CD4$^+$ nadir and other characteristics may have balanced HIV-1 DNA; we further sought to isolate the influence of sex from confounders using multivariate models with relevant characteristics, strengthening our conclusions. Peak pretreatment plasma HIV-1 RNA in women was slightly lower (difference in median 0.13 log, p=0.14), consistent with prior studies reporting lower (0.13-0.35 log) viral loads in women and suggesting that our cohort is representative of a typical pattern of pathogenesis. Although our efforts to match the groups may have attenuated the effect of sex by controlling for factors along the causal pathway our approach focused on reservoir in clinically comparable groups to highlight any direct role of biological sex.

Despite no substantial differences in HIV-1 DNA levels, we observed consistently lower CA msRNA and plasma HIV-1 RNA levels in women. One possible mechanism would be a sex difference in the quality of the DNA reservoir. Whether the higher induction of type 1 interferons in women can amplify hypermutation machinery increasing the proportion of defective HIV genomes in women is unknown. Sequencing of HIV-1 proviruses is warranted to test this hypothesis.

Alternatively, in vivo exposure to estrogen is a potential mechanism for the observed differences in ex vivo measures of virus activity. Estrogen represses HIV-1 transcription in latency models and patient cells and in vitro infection systems, indicating a direct role for hormones in mediating sex differences. We estimated that there was no substantial difference in the short-term TILDA measure of inducible HIV-1 RNA in vitro, but with a wide confidence interval, precluding a strong conclusion. Using a modified EDITS assay we demonstrated HIV induction and replication in a spreading viral infection was potently blocked by estrogen in samples from women. These results are consistent with prior work demonstrating lower per cell HIV RNA production in women in untreated HIV infection and our prior observations of a direct role for the estrogen receptor in maintenance of latency. We observed minimal relationships between virologic and immunologic measures and 17β estradiol at single timepoints; however, a longitudinal approach might better address the impact of the contemporaneous levels of estrogen and progesterone on virus activity.

There were higher levels of immune activation and PD-1 expression in men along with higher levels of CA msHIV RNA and plasma HIV-1 RNA. The PD-1 and HLA-DR/CD38 expression levels in men could be driven by higher levels of stochastic expression of HIV-1 RNA. Alternatively, higher levels of T-cell activation in men (driven by unmeasured confounders or sex-dependent immunologic pathways) could lead to more nonspecific release of inflammatory cytokines that may increase HIV-1 transcriptional activity. It is notable that this sex difference in T cell activation under ART is in contrast to findings during untreated HIV-1 infection, when women have higher levels of T-cell activation for a given level of viremia. Sex differences in PD-1 expression also bear further investigation; in the oncology literature, female sex may be a predictor of response to checkpoint inhibitor therapy.

The exploratory analysis of correlations between immune parameters and virologic outcomes highlighted a few points. The association of the $CD8^+CD27^+28^-45RA^-$ $HLA-DR^+CD38^+$ population with single copy assay values across the cohort and in each sex stratified analyses is notable; this population is an intermediate in the differentiation pathway to an effector memory cell, and cells with this phenotype have both cytokine secretion and cytotoxic capacity. Further studies are necessary to define if these cells are functional and if the positive correlation with low-level residual plasma viremia reveals a direct response to virus or if it reflects a higher state of global activation within the host driven by non-HIV factors. Other notable findings included the positive correlation between the central/effector memory $CD4^+$ $CD27^+CD28^+CD45RA^-HLA-DR^+CD38^-$ and all ex vivo virologic measures. Indeed, there are multiple viral associations with $HLA-DR^+CD38^-$ populations in both $CD4^+$ and $CD8^+$ T-cells. These observations suggest a role for cells with high proliferative capacity or a proliferative milieu of cytokines and growth factors in reservoir maintenance and dynamics, an association that should be explored.

Finally, the sex-stratified immune correlation analysis suggests that there may be distinct relationships between T-cell activation and viral parameters in men and women. The mechanisms and clinical significance of these differences is unclear, but given the focus on immune correlates, a sex difference is important whether it is solely a biomarker or is mechanistically linked. These differences should be considered in small clinical trials with limited enrollment of women where results may be diluted or skewed by sex imbalance. Further, it offers an opportunity to exploit sex differences to determine potential pathways that govern residual virus activity.

In summary, we found that women and men differ in the level of residual virus activity during clinically suppressive ART. A variety of immunological and hormonal mechanisms contribute to this effect. These sex-based differences in HIV reservoir dynamics indicate that sex and hormonal status must be regarded as key parameters in the design and analysis of clinical trials examining HIV-1 eradication strategies.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of determining latent HIV reservoir level in a subject, the method comprising:
   obtaining a blood sample from a HIV+ subject;
   isolating CD4+ T cells from the blood sample;
   administering one or more HIV transcription inducing agents to the isolated CD4+ T cells;
   isolating RNA from the CD4+ T-cells that includes HIV env mRNA, wherein the HIV env RNA is multiple spliced HIV env RNA;
   producing a plurality of first amplicons from the isolated RNA using a first primer set that corresponds to an HIV genomic region encoding the HIV env protein;
   producing a plurality of second amplicons from the plurality of first amplicons using a second primer set, the second primer set including one or more adapter sequences and/or uniquely identifiable barcode sequences;
   determining the nucleic acid sequences of the second amplicons, wherein the determined nucleic acid sequences in the sample are indicative of the amount of inducible cell-associated HIV env RNA in the sample and indicative of the latent HIV reservoir level in the subject.

2. The method of claim 1, wherein the blood sample obtained from the subject includes memory CD4+ T-cells.

3. The method of claim 1, the one or more HIV transcription inducing agents selected from the group consisting of a TCR activating agent, mitogen activation agent, and/or a latency reversing agents.

4. The method of claim 1, the first primer set comprising an external primer set binding to either side of an HIV env RNA splice junction.

5. The method of claim 4, the first primer set including a forward primer having a nucleic acid of SEQ ID NO: 1 and the reverse primer having a nucleic acid of SEQ ID NO: 2.

6. The method of claim 4, the second primer set comprising a forward primer having a nucleic acid of SEQ ID NO: 3, and the reverse primer having a nucleic acid of SEQ ID NO: 4.

7. The method of claim 1, the step of determining the nucleic acid sequences of the second amplicons comprising deep sequencing.

8. The method of claim 1, wherein the subject has been administered highly active antiretroviral therapy (HAART).

9. The method of claim 1, further comprising administering a therapeutically effective amount of one or more HIV therapeutics to the subject having HIV based on the determined latent HIV reservoir level in a subject.

10. The method of claim 9, the one or more HIV therapeutics selected from the group consisting of antiretroviral agents, latency reversing agents (LRAs), selective estrogen receptor modulators (SERMs), HIV/AIDS antivirals, immunomodulators, anti-infectives and/or vaccines.

11. The method of claim 1, wherein the uniquely identifiable barcode sequences are used during the step of determining the nucleic acid sequences of the second amplicons to organize sequence reads into read-families to derive consensus sequences, the consensus sequences increasing the accuracy of allele identification and permitting accurate quantitation and identification of specific sequences in the sample.

12. A method of determining the efficacy of latency reversal agents for reactivating latent HIV-1 reservoirs, the method comprising:
   administering one or more candidate latency reversal agents to a sample of isolated CD4+ T cells;
   isolating RNA from the CD4+ T-cells that includes HIV env mRNA, wherein the HIV env RNA is multiple spliced HIV env RNA;
   producing a plurality of first amplicons from the isolated RNA using a first primer set that corresponds to an HIV genomic region encoding the HIV env protein;
   producing a plurality of second amplicons from the plurality of first amplicons using a second primer set, the second primer set including one or more adapter sequences and/or uniquely identifiable barcode sequences;
   determining the nucleic acid sequences of the second amplicons, wherein the determined nucleic acid sequences in the sample are indicative of the amount of HIV RNA+ cells in the sample; and wherein the increase in HIV RNA+ cells compared to a control is indicative of an effective latency reversal agent.

13. The method of claim 12, wherein the control is a calibration curve generated by cell sorting known numbers of TCR activated primary memory CD4+ T-cells infected with a replication-competent HIV-1 virus carrying a reporter gene.

14. The method of claim 12, wherein the sample of isolated CD4+ T cells includes memory CD4+ T-cells obtained from a subject's blood sample.

15. The method of claim 12, the first primer set comprising an external primer set binding to either side of an HIV env RNA splice junction.

16. The method of claim 15, the first primer set including a forward primer having a nucleic acid of SEQ ID NO: 1 and the reverse primer having a nucleic acid of SEQ ID NO: 2.

17. The method of claim 12, the second primer set comprising a forward primer having a nucleic acid of SEQ ID NO: 3, and the reverse primer having a nucleic acid of SEQ ID NO: 4.

18. The method of claim 12, the step of determining the nucleic acid sequences of the second amplicons comprising deep sequencing.

19. The method of claim 12, wherein uniquely identifiable barcode sequences are used during the sequencing step to organize sequence reads into read-families to derive consensus sequences, the consensus sequences increasing the accuracy of allele identification and permitting accurate quantitation and identification of specific sequences in the sample.

20. The method of claim 12, wherein the sample of CD4+ T-cells is obtained from one or more HIV+ subjects that have been administered highly active antiretroviral therapy (HAART).

21. The method of claim 12, wherein the sample of isolated CD4+ T cells is obtained from a female subject's blood sample.

22. The method of claim 21, further comprising measuring a level of estrogen in the female subject.

23. The method of claim 21, further comprising administering to the sample a selective estrogen receptor modulator (SERM) in addition to the candidate latency reversal agent.

24. The method of claim 23, wherein the SERM is 17β-estradiol.

* * * * *